US009668750B2

(12) United States Patent
Mirochinik et al.

(10) Patent No.: US 9,668,750 B2
(45) Date of Patent: Jun. 6, 2017

(54) BONE MATERIAL REMOVAL DEVICES

(71) Applicant: T.A.G. Medical Devices - Agriculture Cooperative Ltd., Kibbutz Gaaton (IL)

(72) Inventors: Aryeh Mirochinik, Akko (IL); Hagay Sitry, Kibbutz Gesher HaZiv (IL); Rafi Haziza, Kiryat-Bialik (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 0 days.

(21) Appl. No.: 14/919,921

(22) Filed: Oct. 22, 2015

(65) Prior Publication Data

US 2016/0038157 A1 Feb. 11, 2016

Related U.S. Application Data

(63) Continuation of application No. PCT/IL2014/050381, filed on Apr. 24, 2014.

(60) Provisional application No. 61/815,714, filed on Apr. 24, 2013, provisional application No. 61/859,214, filed on Jul. 27, 2013, provisional application No. 61/903,082, filed on Nov. 12, 2013.

(51) Int. Cl.
*A61B 17/00* (2006.01)
*A61B 17/16* (2006.01)
*A61B 17/17* (2006.01)

(52) U.S. Cl.
CPC ...... *A61B 17/1617* (2013.01); *A61B 17/1796* (2013.01)

(58) Field of Classification Search
CPC combination set(s) only.
See application file for complete search history.

(56) References Cited

U.S. PATENT DOCUMENTS

| 3,540,324 A | 11/1970 | Johansson |
| 3,690,357 A * | 9/1972 | Roberto ............... B27G 13/14 144/134.1 |
| 3,702,611 A | 11/1972 | Fishbein |
| 4,710,070 A | 12/1987 | Alsen et al. |

(Continued)

FOREIGN PATENT DOCUMENTS

| EP | 1535579 | 6/2005 |
| EP | 1785103 | 5/2007 |

(Continued)

OTHER PUBLICATIONS

International Search Report and the Written Opinion Dated Sep. 10, 2014 From the International Searching Authority Re. Application No. PCT/IL2014/050381.

(Continued)

*Primary Examiner* — Sameh Boles

(57) ABSTRACT

The present invention in some embodiments thereof, relates to bone material removal devices (2100), for example, devices which change effective diameter. In some embodiments, a bone removal device comprises an expandable portion. In some embodiments, the expandable portion comprises one or more bone removing elements such as cutting teeth (2106). In some embodiments, a cutting tooth is movable between an open position, in which it is configured to widen a bore in a bone, and a closed position. In some embodiments, a cutting tooth of the bone removal device is formed with a curved, such as convex, cutting face (2114).

20 Claims, 31 Drawing Sheets

(56) References Cited

U.S. PATENT DOCUMENTS

| | | | |
|---|---|---|---|
| 5,681,320 A | 10/1997 | McGuire | |
| 6,358,251 B1 | 3/2002 | Mirza | |
| 6,383,188 B2 | 5/2002 | Kuslich et al. | |
| 6,679,886 B2 | 1/2004 | Weikel et al. | |
| 6,746,451 B2 | 6/2004 | Middleton et al. | |
| 6,923,813 B2 | 8/2005 | Phillips et al. | |
| 7,097,648 B1 | 8/2006 | Globerman et al. | |
| 7,172,374 B2 | 2/2007 | Burr et al. | |
| 7,179,024 B2 | 2/2007 | Greenhalgh | |
| 7,637,910 B2 | 12/2009 | Schmieding et al. | |
| 7,682,378 B2 | 3/2010 | Truckai et al. | |
| 7,914,545 B2 | 3/2011 | Ek | |
| 7,938,835 B2 | 5/2011 | Boucher et al. | |
| RE42,757 E | 9/2011 | Kuslich et al. | |
| 8,038,679 B2 | 10/2011 | Wieland | |
| 8,048,079 B2 | 11/2011 | Iannarone | |
| 8,388,621 B2 | 3/2013 | Bourque et al. | |
| 2002/0193799 A1 | 12/2002 | Chappuis et al. | |
| 2005/0113836 A1 | 5/2005 | Lozier et al. | |
| 2005/0240193 A1 | 10/2005 | Layne et al. | |
| 2006/0025774 A1 | 2/2006 | Fishbein et al. | |
| 2006/0149268 A1 | 7/2006 | Truckai et al. | |
| 2006/0195112 A1 | 8/2006 | Ek | |
| 2006/0241629 A1 | 10/2006 | Krebs et al. | |
| 2006/0264957 A1 | 11/2006 | Cragg et al. | |
| 2007/0123889 A1 | 5/2007 | Malandain et al. | |
| 2007/0276392 A1 | 11/2007 | Beyar et al. | |
| 2008/0114364 A1 | 5/2008 | Goldin et al. | |
| 2008/0183174 A1 | 7/2008 | Sikora et al. | |
| 2011/0087257 A1 | 4/2011 | To et al. | |
| 2011/0098709 A1 | 4/2011 | Malandain et al. | |
| 2011/0164937 A1 | 7/2011 | Byrne et al. | |
| 2011/0190832 A1 | 8/2011 | Taylor et al. | |
| 2011/0251616 A1 | 10/2011 | Osman et al. | |
| 2012/0245585 A1 | 9/2012 | Kaiser et al. | |
| 2013/0165935 A1 | 6/2013 | Griffiths et al. | |
| 2014/0194880 A1 | 7/2014 | Schmieding et al. | |
| 2014/0257297 A1 | 9/2014 | Koogle, Jr. et al. | |
| 2014/0276844 A1 | 9/2014 | Bourque et al. | |
| 2014/0324052 A1 | 10/2014 | Carrison et al. | |

FOREIGN PATENT DOCUMENTS

| | | |
|---|---|---|
| ES | 2351563 | 2/2011 |
| WO | WO 2013/192080 | 12/2013 |
| WO | WO 2014/089198 | 6/2014 |
| WO | WO 2014/174521 | 10/2014 |
| WO | WO 2016/063279 | 4/2016 |
| WO | WO 2016/162869 | 10/2016 |

OTHER PUBLICATIONS

International Preliminary Report on Patentability Dated Nov. 5, 2015 From the International Bureau of WIPO Re. Application No. PCT/IL2014/050381.

Communication Relating to the Results of the Partial International Search Dated May 19, 2016 From the International Searching Authority Re. Application No. PCT/IL2015/051033.

International Search Report and the Written Opinion Dated Aug. 4, 2016 From the International Searching Authority Re. Application No. PCT/IL2015/051033.

International Search Report and the Written Opinion Dated Oct. 7, 2016 From the International Searching Authority Re. Application No. PCT/IL2016/050370.

Invitation to Pay Additional Fees Dated Aug. 1, 2016 From the International Searching Authority Re. Application No. PCT/IL2016/050370.

\* cited by examiner

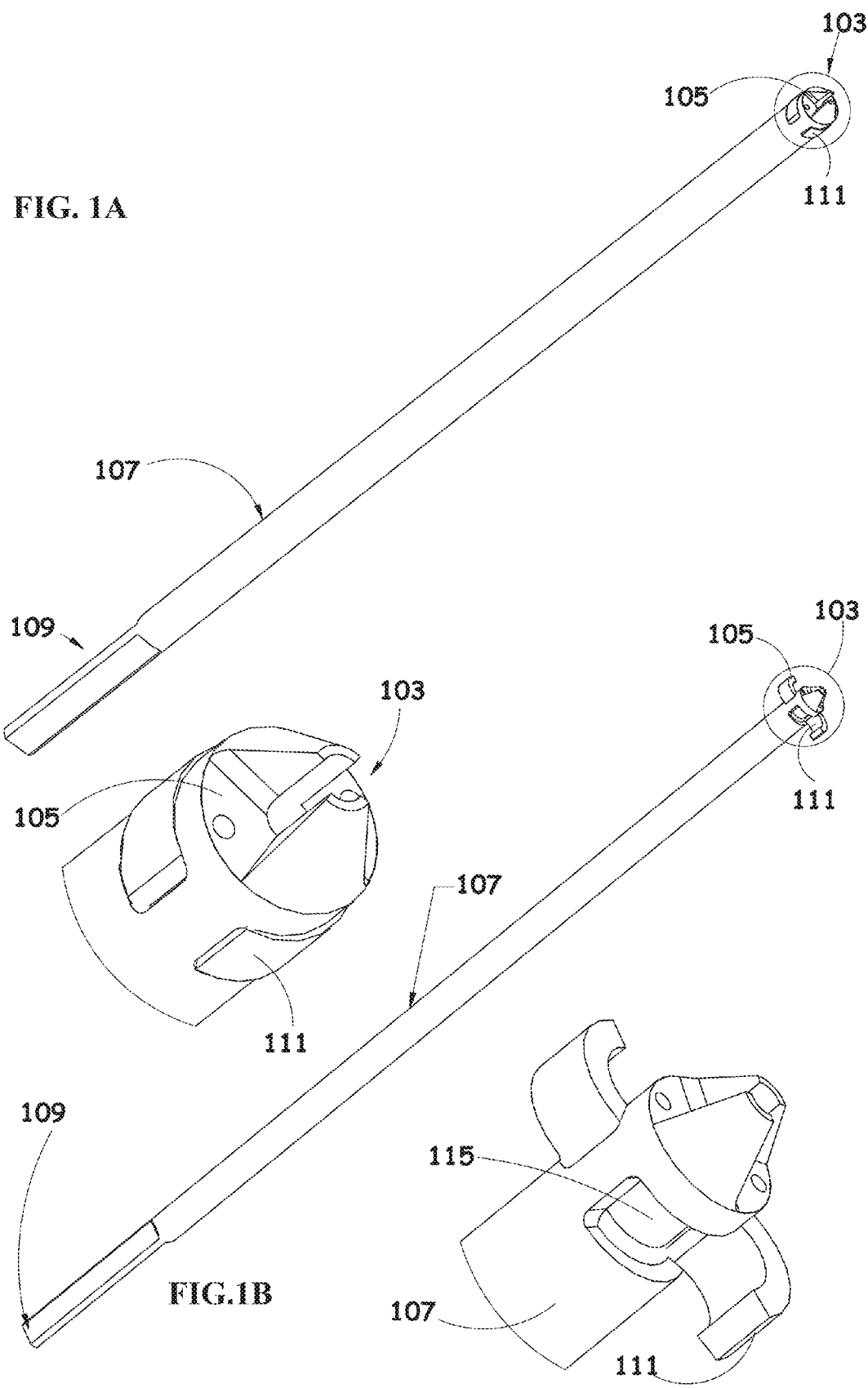

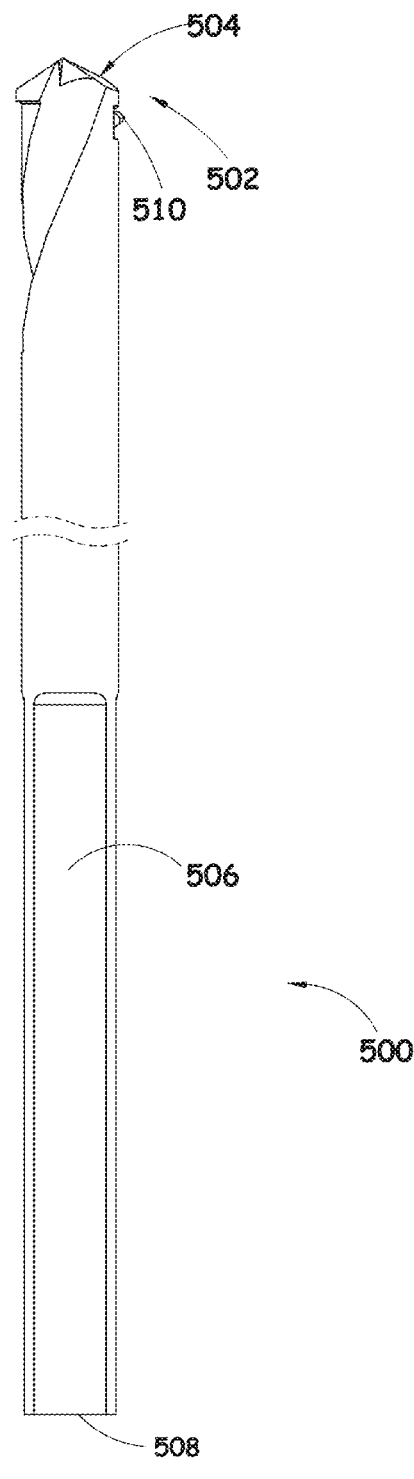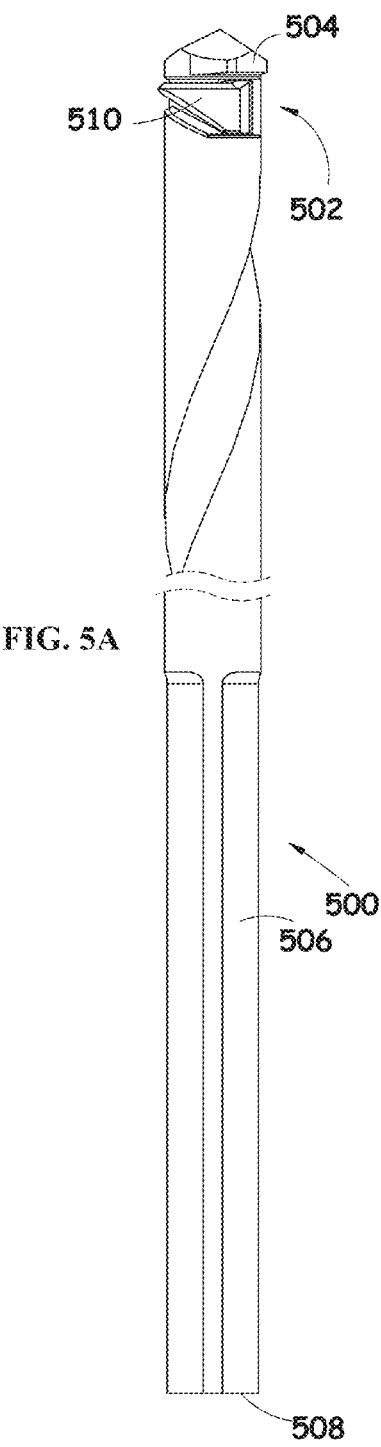

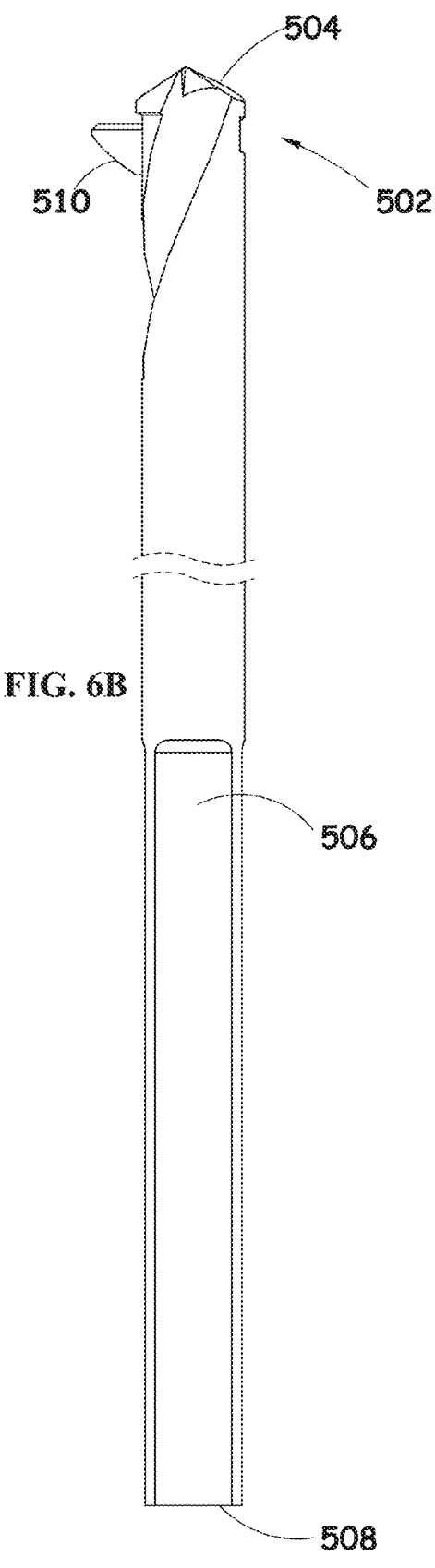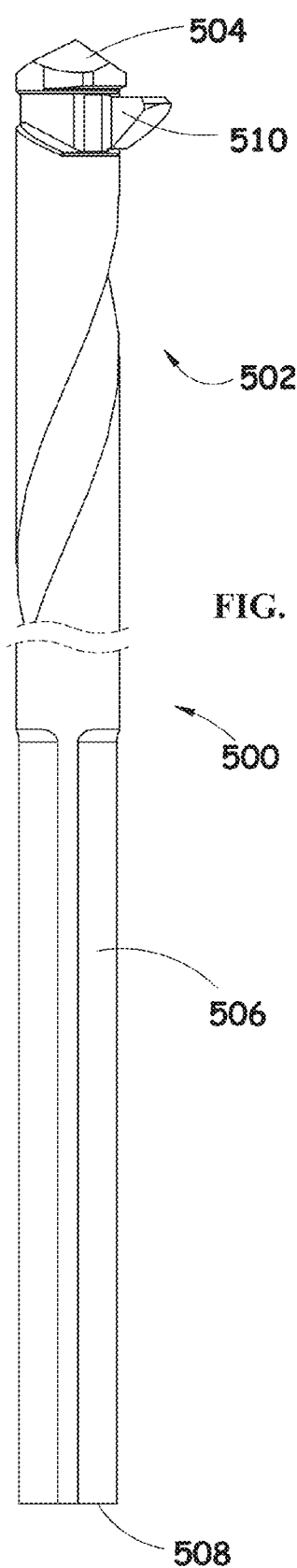

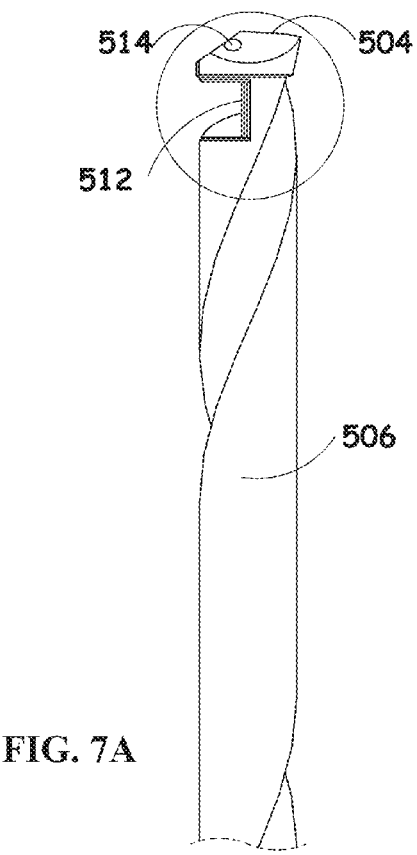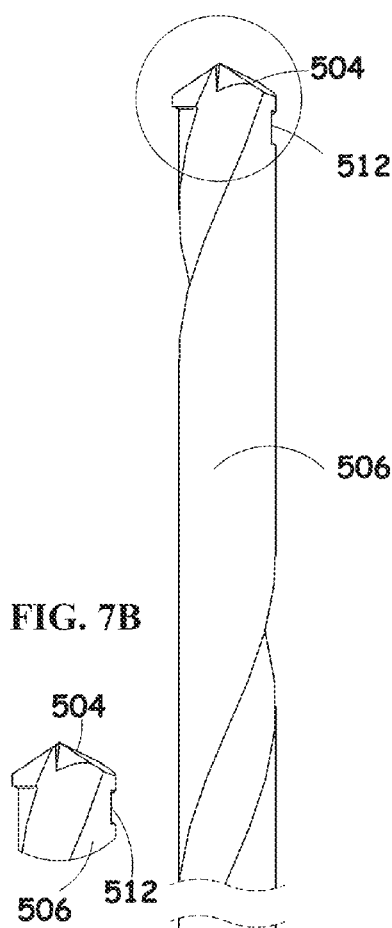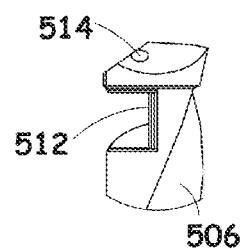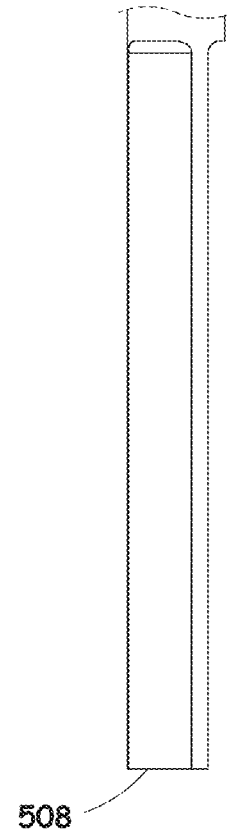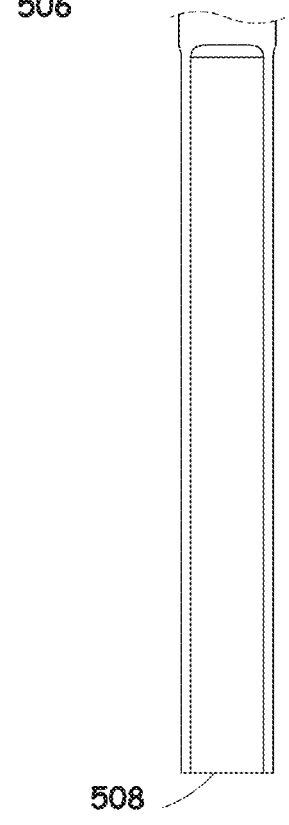
FIG. 7A
FIG. 7B

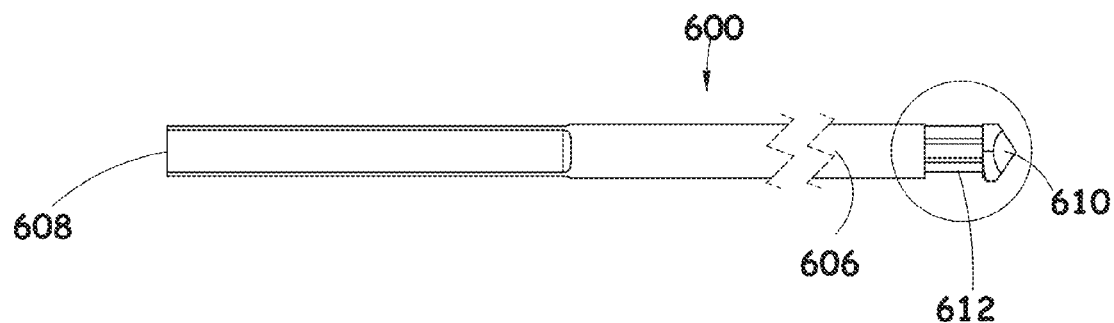
FIG. 15A
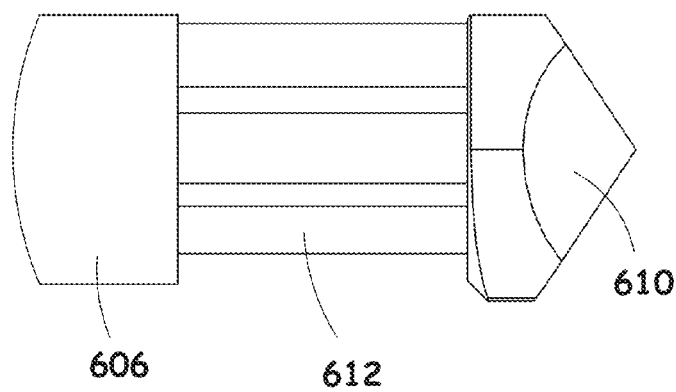
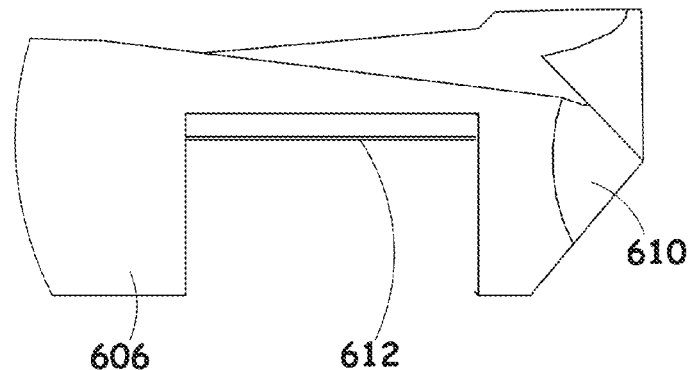
FIG. 15B
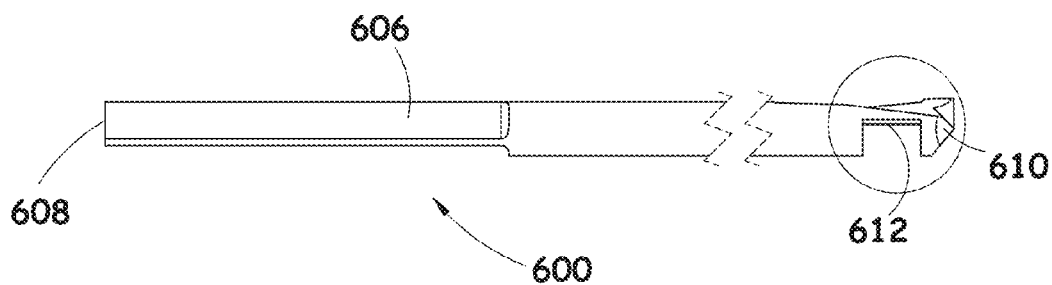

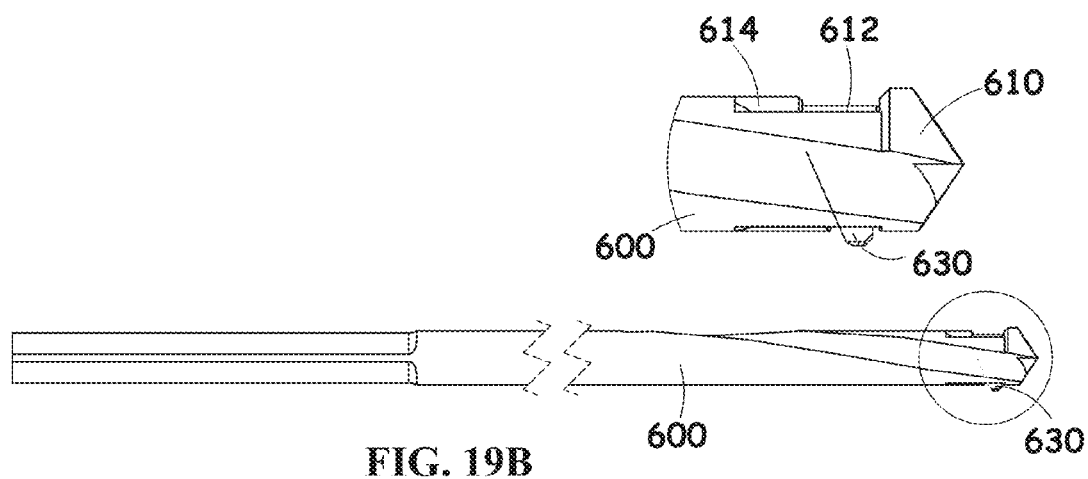
FIG. 19B
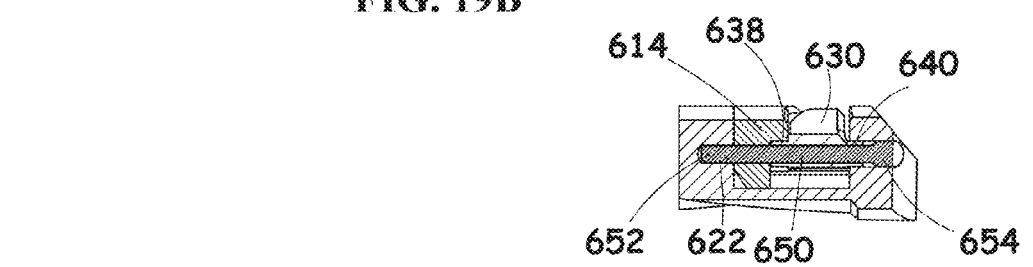
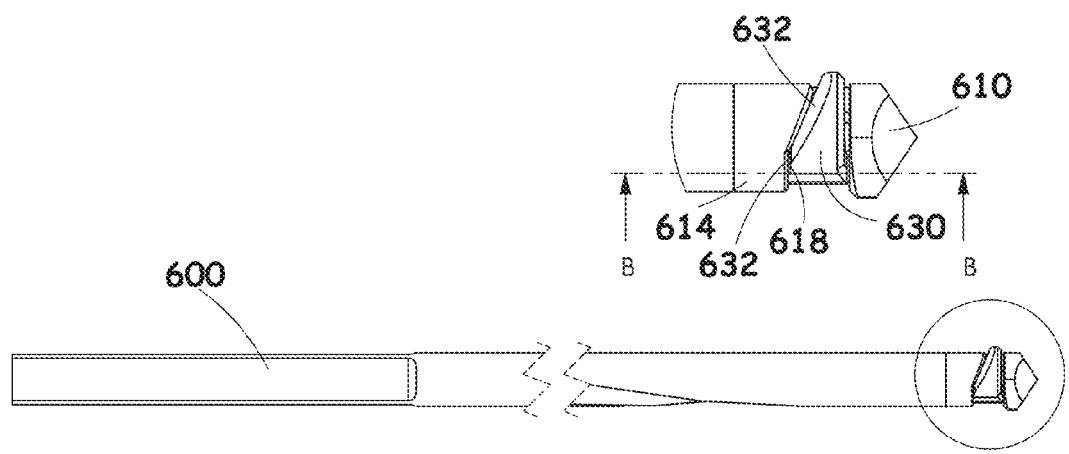
FIG. 19C
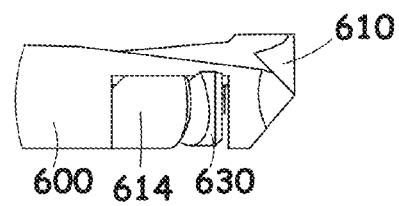
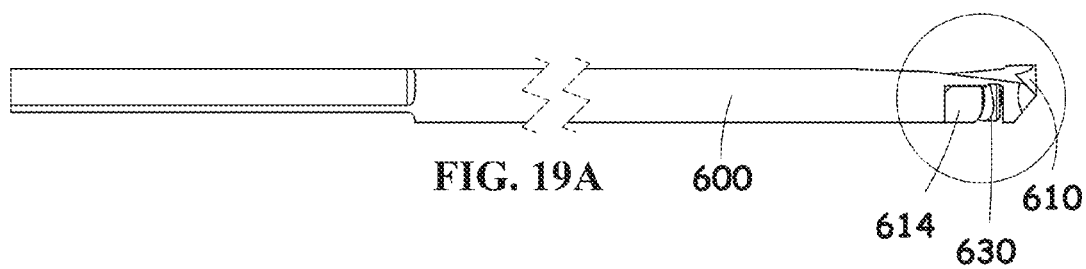
FIG. 19A

BONE MATERIAL REMOVAL DEVICES

RELATED APPLICATIONS

This application is a continuation of PCT Patent Application No. PCT/IL2014/050381 having International filing date of Apr. 24, 2014, which claims the benefit of priority under 35 USC §119(e) of U.S. Provisional Patent Application Nos. 61/815,714 filed on Apr. 24, 2013, 61/859,214 filed on Jul. 27, 2013 and 61/903,082 filed on Nov. 12, 2013. The contents of the above applications are all incorporated by reference as if fully set forth herein in their entirety.

FIELD OF THE INVENTION

The present invention in some embodiments thereof, relates to bone removal tools, for example, tools which change effective diameter.

SUMMARY OF THE INVENTION

According to an aspect of some embodiments there is provided a bone material removal device comprising an elongated shaft, at least one bone material removal element for widening a bore in a bone, the element coupled to the shaft, the element movable from a closed position, in which the element is only partially received within the shaft, to an open position in which the element extends radially away from the shaft, wherein the shaft comprises a section defining a generally cylindrical volume of rotation, and at least a portion of the bone removal element extends beyond the volume of rotation when the element is in the closed position.

In some embodiments, the bone material removal element is a pivotable cutting tooth coupled to the shaft by a hinge.

In some embodiments, the portion of the bone removal element protrudes to a distance ranging between 0.05 mm to 0.5 mm from the volume of rotation of the shaft when in the closed position.

In some embodiments, the cutting tooth comprises a cutting face formed with a concavity. Optionally, a radius of curvature of the concavity ranges between 1.5 mm-4 mm.

In some embodiments, the cutting tooth comprises a cutting face formed with a flat portion.

In some embodiments, the tooth freely pivots on the hinge to open as a result of reversal of rotation direction of the device.

In some embodiments, the hinge comprises proximal and distal elongated extensions received within the shaft to firmly attach the hinge to the shaft.

In some embodiments, the shaft comprises a recess shaped and sized for receiving at least a portion of the tooth, the recess shaped to limit rotational movement of the tooth.

In some embodiments, the device is a drill bit, and the shaft comprises one or more flutes.

In some embodiments, a concavity at the cutting face of the tooth faces a diametrically opposing direction from the flute of the shaft when the tooth is open, to provide an additional path for removal of extracted bone material.

In some embodiments, a bottom surface of the cutting tooth is non-planar to engage an irregular geometry of the bone surface.

In some embodiments, the shaft comprises a tapering head having a pointed distal tip.

In some embodiments, the bone removal element includes at least one supporting element extending in parallel to a longitudinal axis of the shaft and provides for pivotable connection of the bone removal element to the shaft.

In some embodiments, the bone removal element is irremovably attached to the shaft by at least one of a hinge pin or said supporting element.

In some embodiments, the bone removal element extends from the shaft upon rotation due to centrifugal force.

In some embodiments, the bone removal element extends perpendicularly to a longitudinal axis of the shaft.

In some embodiments, the device is adapted to operate in a bore drilling configuration, having a rotation direction in which the bone removal element is in the closed position.

In some embodiments, the device is adapted to operate in a bore widening configuration in which the bone removal element is in the open position. Optionally, the configuration is selected by selecting a direction of rotation.

In some embodiments, the device is cannulated to be inserted over a guide wire.

In some embodiments, the bone removal element extends at least 2 mm beyond the volume of rotation when in the open position.

In some embodiments, the device is a reamer.

In some embodiments, the device comprises a plurality of cutting teeth.

In some embodiments, the device comprises at least one structure configured for resisting further entry of the bone removal element into the shaft in the closed position.

In some embodiments, the structure resisting further entry of said bone removal element into the shaft are one or more walls of a recess in the shaft in which the element is received.

In some embodiments, the structure is an elastic element, allowing for the bone removal element to be pushed into the shaft and be fully concealed within the shaft.

In some embodiments, the bone removal element is a cutting tooth, wherein at least a portion of the cutting tooth is large enough to act as the structure resisting further entry of the tooth into the shaft.

According to an aspect of some embodiments of the invention there is provided a bone material removal kit comprising an elongated shaft, a plurality of cutting teeth, including a first tooth attachable to the shaft, and a second different than the first tooth in at least a radial dimension, the second tooth attachable to the shaft, wherein when one of the teeth is attached to the shaft, the tooth is movable from an open position, in which it extends radially away from the shaft, to a closed position; wherein when the first tooth is in a closed position, the first tooth is at least partially received within the shaft; and wherein when the second tooth is in the closed position, the second tooth is fully received within the shaft.

In some embodiments, the first tooth is larger than the second tooth in at least a radial dimension, so that it contacts side walls of a bore formed in the bone in the closed position.

In some embodiments, the first tooth is configured for opening inside the bore in the bone, utilizing resistance of the walls acting on the tooth.

In some embodiments, the second tooth is configured for opening outside a bore in the bone, utilizing centrifugal force.

According to an aspect of some embodiments there is provided a method for forming a bore in a bone, and widening at least a portion the bore, comprising: inserting a bone material removal device comprising a cutting tooth into a bone, rotating the device in a first direction to form a bore in the bone while at least a portion of the cutting tooth protrudes externally to a shaft of the device, the portion contacting bone tissue at the walls of the bore, when said device is advanced into the bore, reversing the rotation direction of the device, utilizing resistance of the walls of the bore acting on the portion of the cutting tooth to open the tooth, pulling the device through the bore in a direction opposite the insertion direction, to widen at least a portion of the bore using the opened cutting tooth.

In some embodiments, a diameter of the bore is defined by an extent in which the cutting tooth protrudes externally to the device when the tooth is in a closed position.

In some embodiments, the method further comprises advancing the device through the bore until the cutting tooth exits the bone, and reversing a rotation direction to open the cutting tooth utilizing centrifugal force.

In some embodiments, the method further comprises rotating the device in the first rotation direction to close the tooth and remove the device from the widened bore.

In some embodiments, the method further comprises clearing removed bone material in front of the open cutting tooth by means of a curved cutting surface of the cutting tooth.

In some embodiments, a diameter of the bore is widened by at least 30%.

In some embodiments, the device is passed through an existing bore in a bone to widen it.

In some embodiments, inserting comprises drilling. Optionally, drilling comprises drilling using a flexible shaft comprising at least a segment formed with a spring.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B show a bone material removal device comprising an expandable distal tip shown in an open and closed configuration, according to some embodiments of the invention;

FIGS. 5A-5B are two elevation views of a bone material removal device comprising an expandable distal tip, constructed according to another embodiment of the present invention, showing the expandable tip in a closed configuration;

FIGS. 6A-6B are two elevation views of the bone material removal device of FIGS. 5A-5B, showing the expandable tip in an expanded configuration, according to some embodiments of the invention;

FIGS. 7A-7B are two elevation views of a drill of the bone removal device of FIGS. 5A-6B, according to some embodiments of the invention;

FIGS. 15A-15B are two elevation views of a drill of a bone removal device similar to the bone removal device shown in FIGS. 5A-5B, constructed according to yet another embodiment of the present invention;

FIGS. 19A-19B are two elevation views and corresponding enlargements of an assembled bone removal device, showing the expandable tip in a closed configuration, according to some embodiments of the invention;

FIG. 19C is an elevation view, enlargement and a section view of the assembled bone removal device, showing the expandable tip in a closed configuration, according to some embodiments of the invention;

DESCRIPTION OF SPECIFIC EMBODIMENTS OF THE INVENTION

Figure 2A:
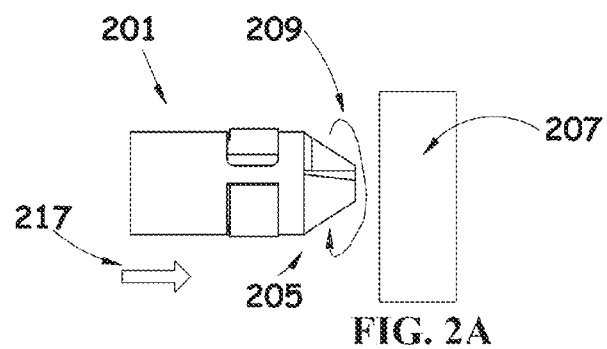
FIGS. 2A-F are a set of drawing showing an exemplary method for drilling a bore in a bone, and widening at least a portion of the bore, according to some embodiments of the invention.

The present invention in some embodiments thereof, relates to bone material removal tools, for example, tools in which an effective diameter of the tool is selectable.

An aspect of some embodiments of the invention relates to a bone material removal device comprising a shaft with an expandable distal portion. In some embodiments, the expandable distal portion comprises one or more bone removing elements, for example cutting or reaming teeth. In some embodiments, the device is adapted to operate in one of two operational configurations, for example one for drilling and/or passing through a bore in a bone, and the other for widening a bore in a bone. In some embodiments, the first configuration comprises cutting teeth at a closed configuration, such as contained within a shaft of the device. In some embodiments, the second configuration comprises cutting teeth at an open configuration, for example extending beyond the circumference of the shaft.

An aspect of some embodiments relates to a bone material removal device comprising a cutting tooth which is only partially received within a recess of a shaft of the device when the tooth is in the closed position.

In some embodiments, the tooth extends beyond a periphery of the device, for example beyond a periphery of a shaft portion configured directly above and/or below the recess in which the tooth is received. In some embodiments, a least a section of the shaft defines a generally cylindrical volume of rotation, and at least a portion of the closed tooth extends beyond the volume of rotation. In some cases, a diameter of a bore formed using the device is defined by an extent in which the tooth protrudes externally to the shaft of the device.

In some embodiments, the tooth is moved to an open position by utilizing resistance of the walls of the bore acting on the protruding portion of the tooth. Optionally, pivoting of the tooth is actuated by reversal of rotation direction of the device, creating friction between the protruding portion of the tooth and the walls of the bore. Alternatively, for example in cases in which the device is inserted into a pre-formed bore in the bone, simply rotating the device (such as without reversing a direction of rotation) would open the tooth.

Additionally or alternatively, in some embodiments, the tooth is advanced passed the bore to exit the bone, and pivoting of the tooth is actuated by reversal of rotation direction, utilizing centrifugal force to open the tooth.

In some embodiments, the recess in the shaft, in which a portion of the tooth is received, is shaped and/or sized to limit movement of the tooth, such as rotational movement, for example preventing over-opening and/or over-closing the tooth. Additionally or alternatively, a hinge by which the tooth is coupled to device is configured for limiting movement of the tooth, for example by comprising one or more transversely extending projections.

In some embodiments, the hinge is a rod hinge, comprising elongated proximal and/or distal extensions that are received within a shaft of the device. A potential advantage of a hinge comprising elongated extensions may include reducing a risk of disengagement of the hinge from a shaft of the device.

An aspect of some embodiments relates to a bone cutting tooth comprising a cutting face formed with a curvature. In some embodiments, at least a portion of the cutting face is concave. Additionally or alternatively, a portion of the cutting face is planar.

In some embodiments, a curved cutting surface such as a concave cutting surface is effective to distribute force applied onto the cutting face by the bone tissue that is being cut. Optionally, the concavity is non-symmetrical, for example along a height of the tooth. Alternatively, the concavity is symmetrical. In some cases, the concavity of the cutting face acts as flute, providing a path for removal of the removed bone material, including, for example, bone chips and/or dust. In some cases, removed bone material flows towards a center of the concavity, and then flows in the proximal and/or distal directions over the top and/or bottom surfaces of the cutting tooth. In some cases, removed bone material exits through a first and/or second openings of the formed bore. Additionally or alternatively, removed bone material is swept by the cutting face towards the walls of the bore.

In some embodiments, a bottom surface of the cutting tooth facing a generally proximal direction is formed with a curvature and/or an inclination, for engaging an irregular bone surface, for example before the opened cutting tooth is pulled back through the bore to widen at least a portion of the bore.

In some embodiments, a back wall of the tooth, such as a generally opposite wall to the cutting face, comprises a rounded geometry so that it is at least partially flushed with the shaft when the tooth is in a closed configuration. In some embodiments, the back wall is curved, and does not inflict resistance to rotation of the shaft when the tooth is closed, for example by smoothly sliding across the walls of the bore during rotation of the shaft.

In some embodiments, the tooth is rigid. In some embodiments, the tooth is elastic enough so that the protruding portion of the tooth is pushed into the recess in the shaft during formation of the bore. Optionally, when the rotation direction changes, the protruding portion immediately bounces out of the shaft, contacting the walls of the bore which thereby initialize the opening of the tooth. Optionally, the tooth continues to pivot to a fully open configuration as rotation continues and increasing resistance is applied to the tooth by the walls of the bore.

In some embodiments, a portion of the tooth, such as a cutting surface of the tooth, is formed of a rigid material. Additionally or alternatively, a portion of the tooth, for example a back wall, is formed of a flexible material.

In some embodiments, the cutting tooth comprises one or more slots or channels, for example the cutting face may be formed with a radially extending slot, through which removed bone material can pass to be cleared away from tooth.

In some embodiments, the cutting teeth extend from the distal tip, for example extending substantially perpendicularly to the longitudinal axis of the device. Optionally, a cutting tooth pivots to an open position, in which it extends radially away from the device. In some embodiments, expanding the distal portion includes enlarging a radius of the bone engaging portion of the device. In some embodiments, the device includes a forward drill bit.

In an exemplary embodiment of the invention, the bone removal elements are attached to the shaft freely enough so that rotation of the shaft at sufficient speed would cause them to extend radially outwards from a position they are in, for example from a position in which the elements are flush with the shaft or a position in which the elements are recessed from the shaft. In an exemplary embodiment, the shaft includes a stop which prevents over extension of the elements, for example, limiting the rotation of the elements around a hinge which attaches them to the shaft to an angle ranging between, for example, 50, 70, 80, 90, 100 or smaller or intermediate or greater number degrees.

In some embodiments, a stopping element is configured to restrict entry of a cutting element further into the shaft, for example when the cutting element is in a closed position. In some embodiments, the stopping element comprises one or more walls of a recess in the shaft in which the bone removal element is received. In some embodiments, the stopping element is the cutting element itself, for example being formed with a portion large enough to prevent the cutting element from fully entering the shaft. In an example, a radial extent of a cutting element is larger than that of the shaft, preventing from the complete cutting element to be fully contained within the shaft. In some embodiments, the stopping element comprises an elastic element such as a spring coupled to the tooth and/or the shaft, which allows for the cutting element to be pushed into the shaft. Optionally, the spring provides for the cutting element to bounce open, for example to form contact between the cutting element and the walls of the bore in the bone. Optionally, friction is created between the cutting element and the walls, actuating initial opening or further opening of the tooth.

In some embodiments, the operational configuration is selected by a user. In some embodiments, changing the direction of rotation causes the cutting teeth to extend, such as by pivoting to an open configuration, or alternatively to fold back into a closed configuration. For example, this may be provided by the relative locations of a center of gravity of the tooth and a hinge (e.g. an axial pin) connecting the tooth to the shaft. In some embodiments, centrifugal force created during the rotation of the device thrusts the cutting teeth outwardly from the shaft of the device.

In some embodiments, rotation causes extension, obtained for example by pivoting of a tooth with respect to a shaft of the device, until reaching a stop. However, the teeth may be free to move back to a previous position. In such a case, the extension (such as by pivoting) of the teeth will depend on the direction of rotation and existence of nearby objects, such as bone, to contact the teeth. Rotation in a first direction will cause the teeth to engage the bone, and the stop will prevent the teeth from moving out of the way, ultimately resulting in bone removal. A rotation in opposite direction allows the tooth to retreat from the force applied by the bone, and possibly fold back to become flush with the shaft.

In some embodiments, the device can be seen as having two behaviors, depending on the drilling direction. In one drilling direction, contact of extended teeth with objects such as bone will tend to close the teeth, and in the other drilling behavior the teeth, when contacting bone, will tend to remain in an extended position and remove bone material.

In some embodiments, an initial bore is drilled in a bone. In some embodiments, after the initial bore is drilled, the device is used for widening at least a portion of the bore. In some embodiments, by reversing the direction of rotation of the device, the cutting teeth are pushed outward. In one example, when the device is rotated in a clockwise direction the cutting teeth are maintained within the circumference of the shaft of the device, and when the device is rotated in a counterclockwise direction the teeth extend outwardly from the shaft. Optionally, the centrifugal force created once the direction of rotation is reversed is strong enough to thrust the cutting teeth outwards.

In some embodiments, the shaft of the device comprises a flexible portion, for example comprising a spring.

An aspect of some embodiments relates to a bone material removal kit, comprising a device for example as described herein, and a plurality of replaceable cutting teeth. In some embodiments, the cutting teeth include a first tooth which is only partially received within a shaft of the device, and a second tooth which is fully received within a shaft of the device. In some embodiments, at least a portion of the first tooth, in a closed position, contacts walls of the bore in the bone, to provide for friction based opening of the tooth when the device is inside a bore in the bone. In some embodiments, the second tooth is moved to an open configuration as a result of rotation, for example due to centrifugal force.

Optionally, a user selects the first tooth when opening of the tooth inside the bore is desired, and selects the second tooth when opening of the tooth outside the bore is desired. In some embodiments, the tooth is configured as a part of a unit, for example including a shaft segment which can be assembled onto the device.

FIGS. 1A-B show a bone material removal device 101 comprising an expandable distal portion 103, according to some embodiments of the invention. An enlarged view of distal portion 103 of FIG. 1A and of FIG. 1B is shown under each.

In some embodiments, the device comprises a distal tip 105, a shaft 107, and a proximal end 109.

In some embodiments, a distal portion 103 of the device comprises a plurality of bone removal elements such as cutting teeth 111, for example 1, 2, 5, 8 or any larger or intermediate numbers. In some embodiments, the cutting teeth 111 extend from shaft 107 of the device. In some embodiments, as will be further explained, centrifugal force caused by rotation of the device acts on the cutting teeth to extend them.

In some embodiments, the device is adapted to two operational configurations. In the first configuration, shown in FIG. 1A, the cutting teeth remain in a closed configuration, for example contained within a circumference of the shaft. In the second mode, shown in FIG. 1B, the cutting teeth extend externally from the shaft to an open configuration, for example extending beyond the circumference of the shaft. In some embodiments, the drilling direction is compatible with the closed configuration. In some embodiments, the drilling direction is compatible a configuration in which the teeth, once open, will close rather than stay open.

In some embodiments, the first operational configuration shown in FIG. 1A is used for drilling a bore in a bone. Optionally, drilling is performed by attaching proximal end of the device 109 to a drill motor (not shown). In some embodiments, the first configuration is used for passing the device through an existing bore, possibly without rotation. Optionally, a spring element (e.g. between teeth 111 and shaft 107) or a coupling material (e.g. a coating on the elements) is provided to apply a small force to maintain teeth 111 in conformance with the surface of shaft 107.

In some embodiments, in the first operational configuration, cutting teeth 111 are contained within the shaft. In some embodiments, the cutting teeth are positioned at the shaft's circumference. Optionally, in the closed configuration, the cutting teeth do not extend beyond the largest diameter of the shaft. Alternatively, in the closed configuration, the cutting teeth extend beyond the diameter of the shaft.

In some embodiments, the second operational configuration shown in FIG. 1B is used for widening at least a portion of a bore in a bone. In some embodiments, the cutting teeth 111 extend externally from the shaft 107, for example extending perpendicularly to a main axis of the shaft. In some embodiments, when cutting teeth 111 are extended to an open configuration, they increase a diameter of at least one section of the distal portion 103, for example distal tip 105, for example by 20%, 70%, 90% and/or smaller, greater, or intermediate numbers.

In some embodiments, a user may selectively choose the operational configuration, for example by choosing the direction of rotation of the device. In some embodiments, when rotating in one direction, for example in a clockwise direction, the cutting teeth 111 remain adjacent to the shaft in a closed configuration. Additionally and/or alternatively, when rotating in the opposite direction, such as a counter-clockwise direction, centrifugal force causes the cutting teeth 111 to extend beyond the shaft's circumference.

In some embodiments, the rotation always causes extension of the teeth, but the rotational direction decides if the teeth will tend to remain open or close, when contacting an object.

Some embodiments comprise cutting teeth 111 having various shapes and/or sizes of cutting edges, for example a cutting edge having a rectangular cross section, a circular cross section, or a triangular cross section. In some embodiments, cutting teeth are shaped as an arc. Optionally, the length of the arc is a half of the circumference of the shaft. In one example, two arc shaped cutting teeth complete the shaft's circumference. In some embodiments, the arc has a thickness, in an axial and/or radial direction, for example a thickness of 0.2 mm, 0.4 mm, 2 mm, or any smaller, intermediate or larger thicknesses. In some embodiments, the cutting teeth 111 are formed with an eroding exterior, for example to file the bore during widening.

In some embodiments, a cutting tooth 111 is connected to the shaft 107, for example connected using a hinge or a pivot. In some embodiments, the connection area includes a geometry which inhibits free motion of the cutting tooth 111, for example allowing the cutting tooth to extend and open only in one direction. In some embodiments, the degree of pivoting is manufactured according to a need, for example limiting a cutting tooth to open at 30 degrees, 60 degrees, 90 degrees or any intermediate or smaller numbers with respect to the axis of pivoting.

In some embodiments, a section such as section 113, shown in the enlarged version of distal portion 103 in FIG. 1B, prevents cutting tooth 111 from over opening, for example opening in angle larger than 180 degrees.

In some embodiments, shaft 107 comprises a recess 115. Optionally, recess 115 receives a cutting tooth 111, for example when the device is in a closed configuration.

In some embodiments, different teeth have different lengths. In some embodiments, different teeth have different axial positions. For example, one cutting tooth may extend to a length equal to half the circumference of the shaft, while a second cutting tooth may extend to a length that is a quarter of the circumference of the shaft.

In some embodiments, the shape of the cutting teeth and/or the size of their cutting edges and/or faces is selected to create a certain pattern of the widening of the bore.

In some embodiments, the cutting teeth extend in an individual manner, for example each cutting tooth extends independently of another. Alternatively, the cutting teeth may be manufactured so that opening of one tooth to an extended configuration leads to the opening of another tooth, for example by pushing an adjacent tooth.

In some embodiments, cutting teeth may be spring loaded, for example to open or close them.

In some embodiments, the device is a drill. In some embodiments, the device is a reamer.

In some embodiments, the distal tip is a drill bit. Optionally, the distal tip comprises a threaded portion. In some embodiments, the proximal end is shaped to engage a drill, for example having a hexagonal shape.

In some embodiments, the device is cannulated, for example to be inserted over a guiding wire.

In some embodiments, the device comprises a plurality of depth indicating markings.

In some embodiments, the device is made of stainless still, such as Eagle Stainless Steel. In some embodiments, the cutting teeth 111 are made of the same material as the rest of the device, or made of a different material.

FIGS. 2A-D are a set of drawings showing an exemplary method for drilling a bore in a bone, and widening at least a portion of the bore, according to some embodiments of the invention. FIGS. 2E-F are enlarged views of a distal tip of the device during the stages described at FIGS. 2A-B and FIGS. 2C-D respectively.

In some embodiments, device 201 is used for drilling a bore in bone. In some embodiments, as shown in FIG. 2A, one or more cutting teeth 203 are in a closed configuration. In some embodiments, a distal tip of the device 205 is inserted into a bone 207. In some embodiments, distal tip 205 is a drill bit, optionally having a threaded portion. In some embodiments, during insertion into the bone, device 201 is rotated, for example by being connected to a drill, in a direction such as direction 209.

Figure 2B:
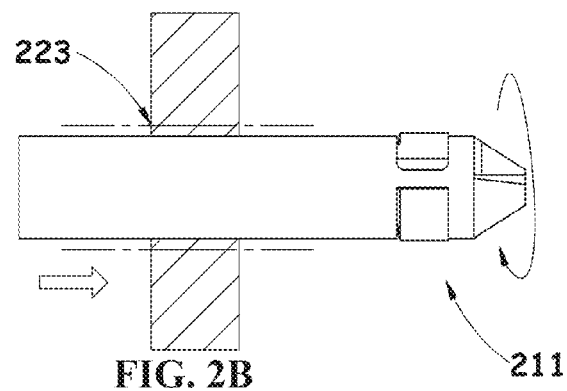

In some embodiments, as shown in FIG. 2B, the device drills through bone 207 to create a bore 223 (marked by the dotted line) extending between opposite sides of the bone. In some embodiments, a distal portion of the device 211 extends beyond bone 207.

In some embodiments, bone 207 prevents cutting teeth 203 from extending. Additionally and/or alternatively, bone 207 forces cutting teeth 203 back to a closed configuration.

Figure 2C:
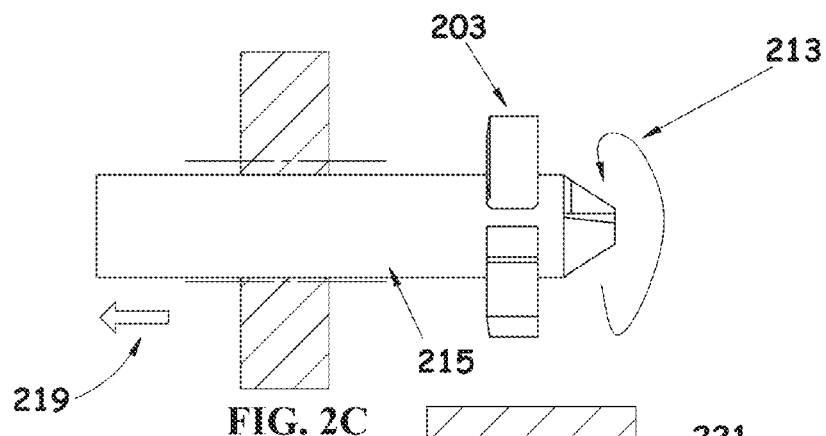

In some embodiments, as shown in FIG. 2C, once a bore has been drilled, cutting teeth 203 are forced to extend externally to shaft 215. In some embodiments, by reversing the direction of rotation to an opposite direction 213, the centrifugal force created acts on cutting teeth 203 so that they extend outwardly from the shaft, such as by pivoting on a hinge. In some embodiments, at this point, the device is pulled (for example using the drill) backwards, such as back into the drilled bore, in the direction shown by arrow 219.

Figure 2D:
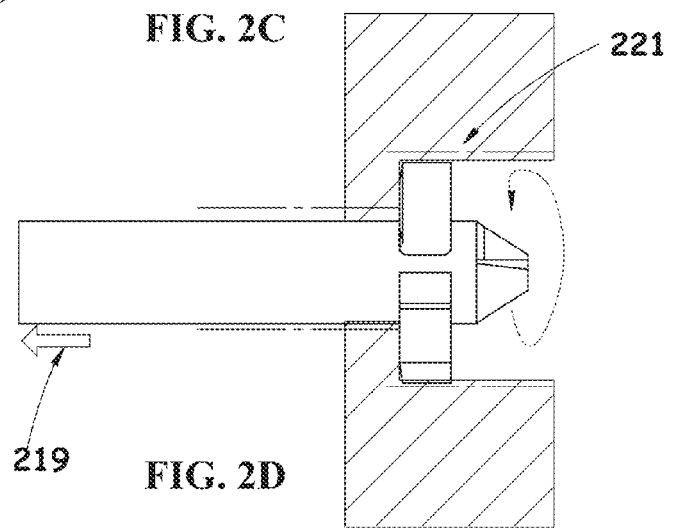
Figure 2F:
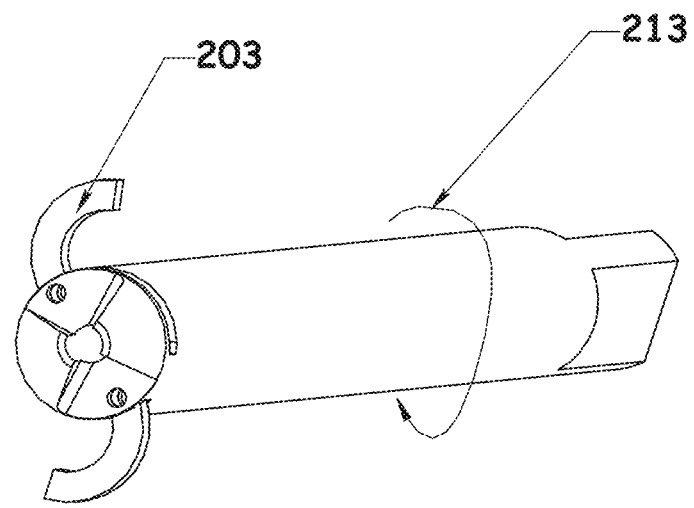
Figure 2E:
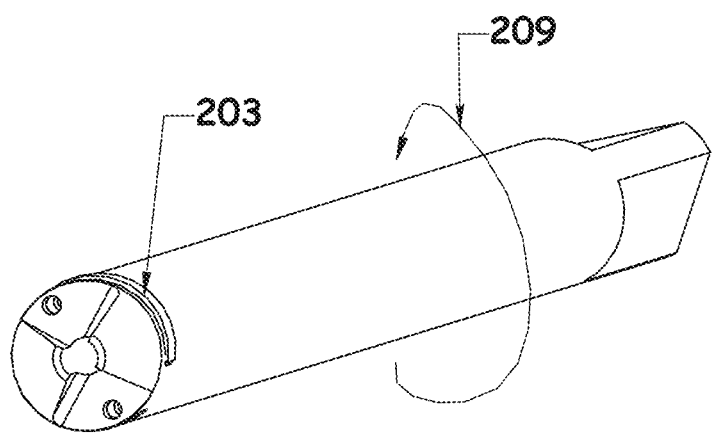

In some embodiments, as shown in FIG. 2D, the reversed direction of rotation retains the cutting teeth 203 in their open configuration. In some embodiments, as the device is pulled backwards through the existing bore, cutting teeth 213 widen a diameter of the bore, as shown in 221. In some embodiments, cutting teeth remove bone material by cutting and/or crumbling the bone tissue. In some embodiments, the initial diameter of the bore widened by 10%, 50%, 90% and or intermediate and/or larger values.

In some embodiments, the cutting teeth 203 remain in their open configuration due to opposite forces exerted by the walls of the bore, for example if the bore is narrow.

In some embodiments, only a portion of the bore is widened. Optionally, the widening of a portion of the bore forms a location to anchor, for example, an ACL or any other ligament or object which may be pulled against a narrow part of the borrow.

In some embodiments, the direction of rotation is reversed again, for example half way through the bore, causing cutting teeth 203 to return to their closed configuration inside the shaft. In some embodiments, a face and/or edge of the cutting tooth is curved, so that contact with the bore applies a radial closing force on the cutting tooth.

In some embodiments, the device is then pulled back through the remaining portion of the bore, optionally without widening it.

In some embodiments, for example if a bore already exists in bone 207, the device may be used to only widen the existing bore, for example by being inserted in a closed configuration through the bore, and pulled back up in an open configuration so that the cutting teeth cut along at least a portion of the existing bore to widen it upon rotation.

The enlarged view in FIG. 2E shows the cutting teeth 203 in closed configuration. Optionally, the device is rotated in the first direction 209.

The enlarged view in FIG. 2F shows the cutting teeth 203 in an open configuration. Optionally, the device is rotated in the second direction 213.

Figure 3:
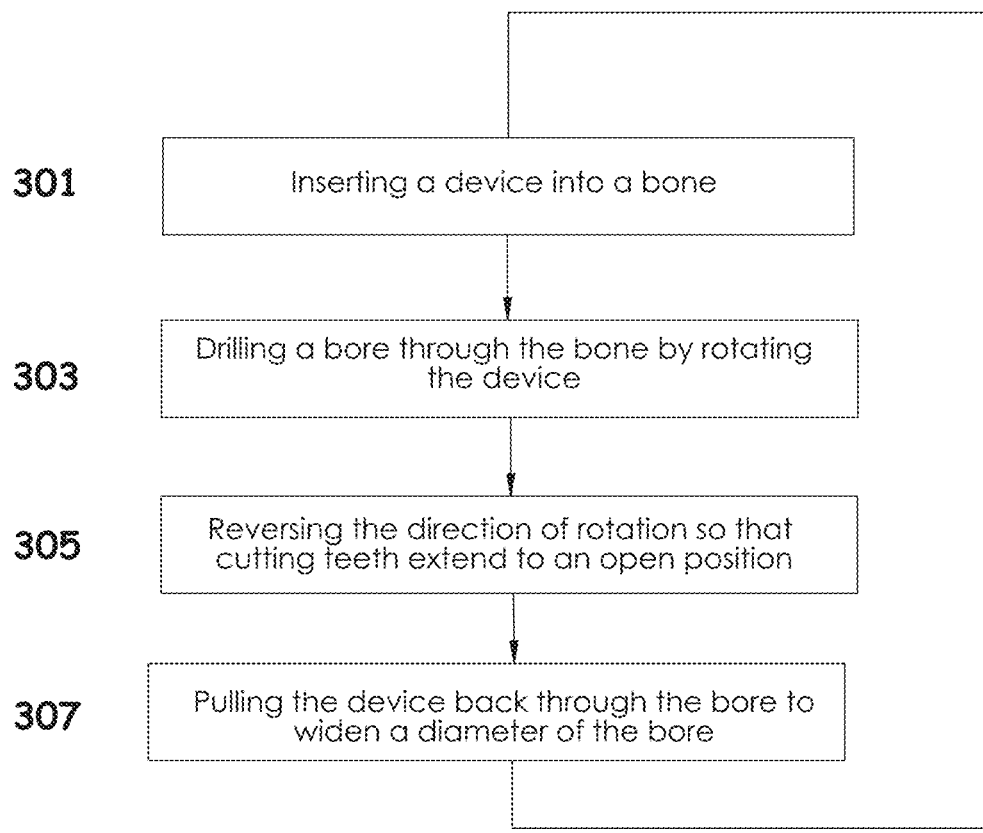
FIG. 3 is a flowchart of an exemplary method for drilling a bore in bone, and widening at least a portion of the bore, according to some embodiments of the invention.

FIG. 3 is a flowchart of an exemplary method for drilling a bore in bone, and widening at least a portion of the bore, according to some embodiments of the invention. In some embodiments, a device is inserted into the bone, 301. In some embodiments, a bore is drilled through the bone using the device 303, for example by rotation of the device. Alternatively, as previously mentioned, the device passes through an existing bore in a bone, for example a bore previously created using a drill or any other means for forming a bore.

In some embodiments, the bore is drilled through a portion of the bone, for example extending to a certain depth within the bone, such as 2 mm, 9 mm, 5 cm, 7 cm and/or any smaller, intermediate or larger depths. In some embodiments, the drilled bore extends between two opposite faces of the bone.

In some embodiments, a distal portion of the device extends beyond an exit aperture of the bore. In some embodiments, this positioning allows the distal portion to be located in a large enough lumen for allowing the cutting teeth to extend into an open configuration. Optionally, a large enough lumen exists in a different location, for example a naturally formed lumen within the bone.

In some embodiments, extension of the cutting teeth is achieved by rotation of the device, for example rotation in an opposite direction to the direction of rotation during drilling of the bore 305. Optionally, a centrifugal force created during rotation is strong enough to thrust the cutting teeth into an open configuration.

In some embodiments, once the cutting teeth are in their open extended configuration, the device may be pulled back though the bore. In some embodiments, the cutting teeth widen the bore as the device is pulled back. Optionally, the rotation speed affects cutting effect of the teeth.

In some embodiments, the device widens a diameter of at least a portion of the bore (307), for example widens a third of the length bore, a half of the length of the bore, or the full length of the bore. In some embodiments, a diameter of the bore may increase by 10%, 50%, 90% and/or intermediate or larger values.

In some embodiments, a user selectively decides not to extend the cutting teeth, for example to avoid widening the bore. Optionally, the device is pulled back through the bore having the teeth in a closed configuration.

Figure 4:
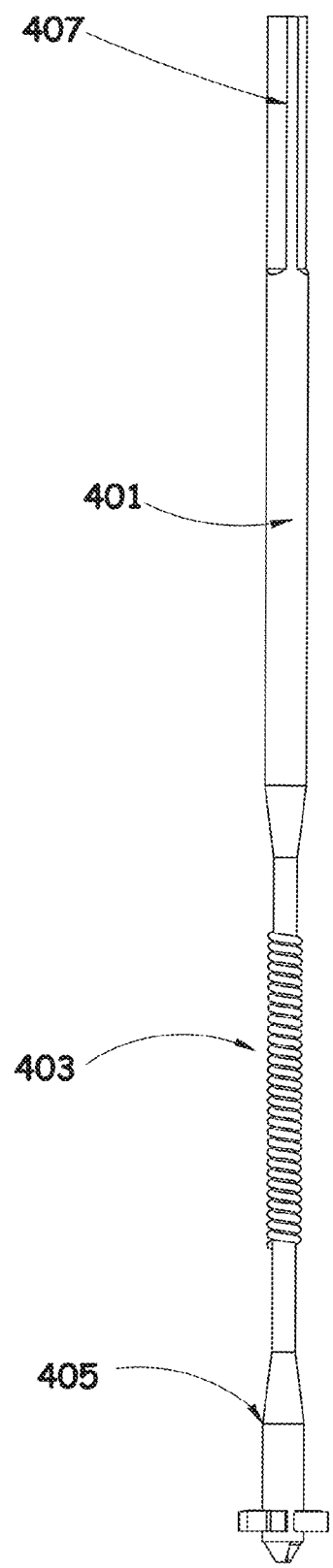
FIG. 4 is a bone removal device comprising an expandable distal tip and a shaft comprising a flexible portion, according to some embodiments of the invention.
Figure 8B:
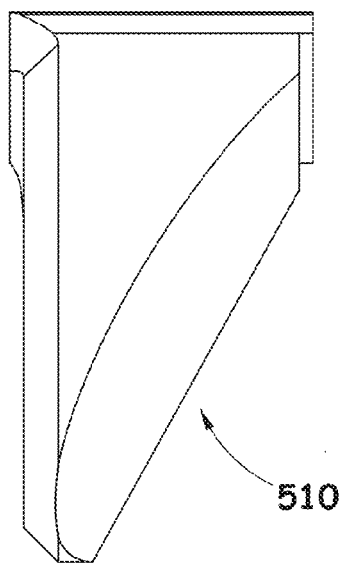
FIGS. 8A-8D are a pictorial view and three different elevation views of a cutting tooth of the bone removal device of FIGS. 5A-6B, according to some embodiments of the invention.
Figure 8D:
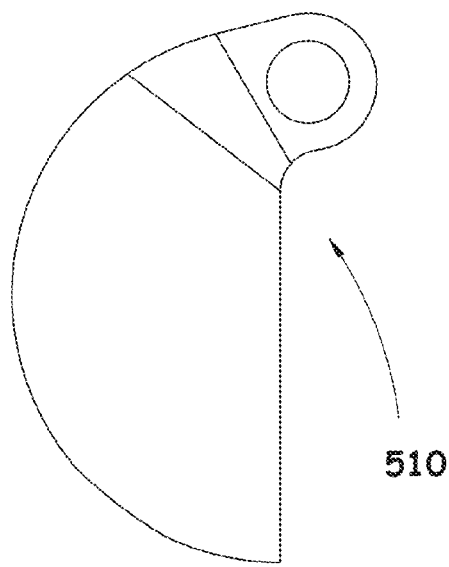
Figure 8A:
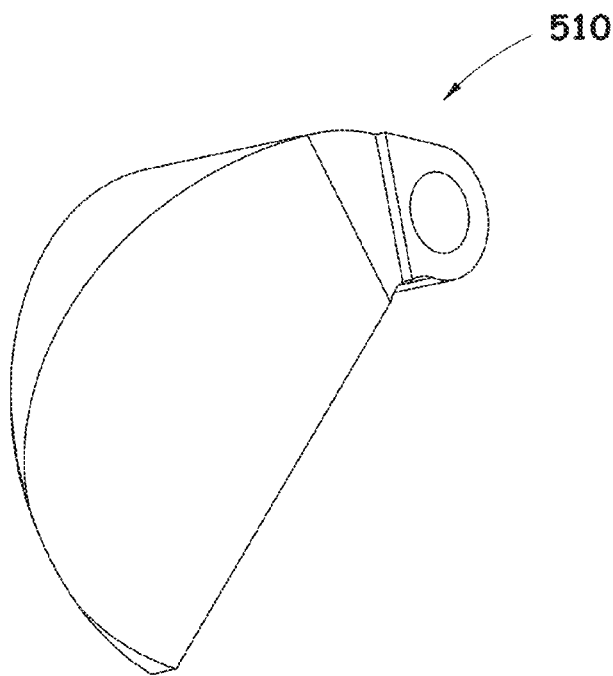
Figure 8C:
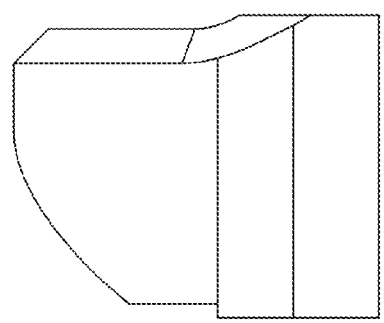

FIG. 4 shows an expandable bone removal device having a shaft with a flexible portion, according to some embodiments of the invention. In some embodiments, shaft 401 comprises a flexible portion 403, extending for example between a distal tip 405 and a proximal end 407, or a segment of that portion.

In some embodiments, flexible portion 403 comprises a spring. Optionally, the spring transmits torque during rotation of the device to distal tip 405.

In some embodiments, distal tip 405 comprises an expandable portion such as cutting teeth 409. In some embodiments, distal tip 405 does not comprise an expandable portion. Optionally, distal tip 405 is a drill bit.

In some embodiments, flexible portion 403 enables bending of the device, for example allowing drilling in bone locations that cannot be approached directly. In some embodiments, for example if the device is bended, a curved bore may be formed. In some embodiments, the device is inserted over a guide wire.

In some embodiments, flexible portion 403 has the same diameter as the rest of shaft 401. In some embodiments, flexible portion 403 has a smaller diameter than the diameter of shaft 401.

In some embodiments, the spring comprising flexible portion 403 is attached to shaft 401 during manufacturing using laser welding techniques and/or other techniques suitable for coupling the spring to the shaft.

Reference is now made to FIGS. 5A-5B, which show a bone material removal device 500 constructed according to another embodiment of the present invention, including an expandable distal portion 502, showing the expandable portion 502 in a closed configuration.

It is seen that the bone material removal device 500 includes a distal tip 504, a longitudinal shaft 506 and a proximal end 508.

The distal portion 502 of the bone material removal device 500 preferably includes a single cutting tooth 510. It is appreciated that the distal portion 502 may include a plurality of cutting teeth 510.

It is a particular feature of some embodiments of the present invention that the cutting tooth 510 extends from the outer circumference of the shaft 506 both in closed configuration and in open configuration, as seen in FIGS. 5A-5B and FIGS. 6A-6B.

In an exemplary embodiment of the present invention, centrifugal force and friction force between the cutting tooth 510 and a portion of the bone cause the expandable portion 502 to open and thus the cutting tooth 510 extends further from the longitudinal shaft 506, as will be described in detail below.

The device is adapted for two operational configurations.

The first configuration is shown in FIGS. 5A-5B, where the cutting tooth 510 remains in a closed configuration, such that only a small portion of cutting tooth 510 extends out of the outer circumference of the longitudinal shaft 506. In an exemplary embodiment of the present invention, the cutting tooth 510 extends approximately 0.1 mm from the outer circumference of the shaft 506.

The second configuration is shown in FIGS. 6A-6B, where the cutting tooth 510 extends externally from the outer circumference of the shaft 506 to a greater extent, assuming an open configuration of the bone material removal device 500.

The first operational configuration shown in FIGS. 5A-5B is typically used for drilling a bore in a bone. Optionally, drilling is performed by attaching proximal end 508 of the device 500 to a drill (not shown). In some embodiments, the first configuration is used for inserting the device 500 into an existing bore, possibly without rotation.

According to an exemplary embodiment of the invention shown in FIGS. 5A-5B, in the first operational configuration, cutting tooth 510 slightly extends from the outer circumference of the shaft 506.

According to an exemplary embodiment of the invention shown in FIGS. 6A-6B, the second operational configuration is used for widening at least a portion of a bore in a bone. In some embodiments, the cutting tooth 510 extends externally from the outer circumference of the shaft 506, for example extending perpendicularly to a main axis of the shaft to a greater extent than in the first operational configuration shown in FIGS. 5A-5B. In some embodiments, when cutting tooth 510 is extended to an open configuration, it increases a diameter of at least one section of the distal portion 502, for example distal tip 504, for example by 20%, 70%, 90% and/or any smaller, greater, or intermediate numbers.

A user may selectively choose the operational configuration, for example by choosing the direction of rotation of the bone material removal device 500. In some embodiments, when rotating in one direction, for example in a clockwise direction, the cutting tooth 510 remains adjacent to the shaft 506 and slightly extending therefrom in a closed configuration. Additionally and/or alternatively, when rotating in the opposite direction, such as a counterclockwise direction, frictional force formed between the bone portion and the portion of the cutting tooth 510 which extends beyond the circumference of the shaft 506 and centrifugal force cause the cutting tooth 510 to extend to a greater extent beyond the circumference of the shaft 506.

Reference is now made to FIGS. 7A-7B, which show the drill of the bone material removal device 500 constructed in accordance to an exemplary embodiment of the present invention, consisting of a longitudinal shaft 506 having a proximal end 508, distal tip 504 and a recess 512 for insertion of a cutting tooth 510 therein. In some embodiments, distal tip 504 is a drill bit, optionally having a threaded portion.

It is seen in FIGS. 7A-7B that the drill is cannulated, including a longitudinal bore 514 extending from the distal end 508 to the proximal tip 504 for flushing or removal of residual drilling materials.

FIGS. 8A-8D illustrate an exemplary design of a cutting tooth 510 insertable into recess 512 of the drill of the bone material removal device 500.

Figure 9C:
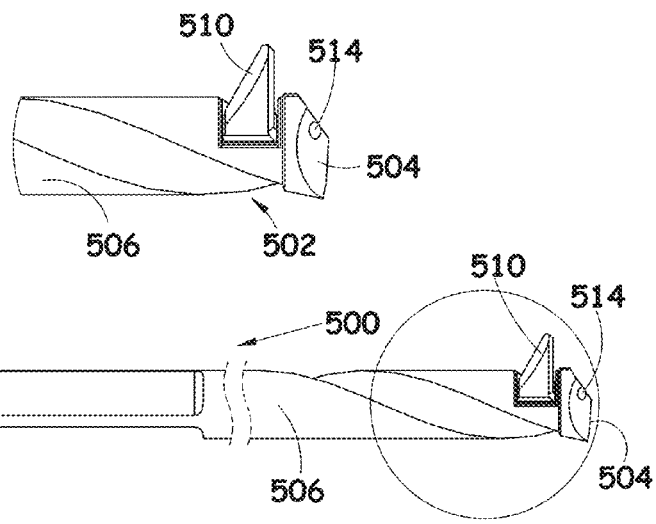
FIG. 9C is a pictorial view and an enlargement view of the bone material removal device of FIGS. 5A-6B in an expanded configuration, according to some embodiments of the invention.
Figure 9B:
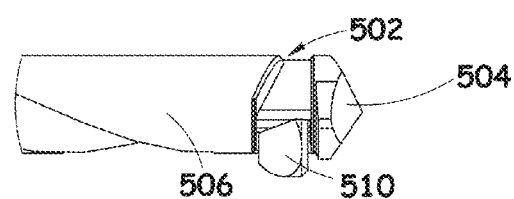
FIG. 9B is a pictorial view and an enlargement view of the bone material removal device of FIGS. 5A-6B in a partially open configuration, according to some embodiments of the invention.
Figure 9A:
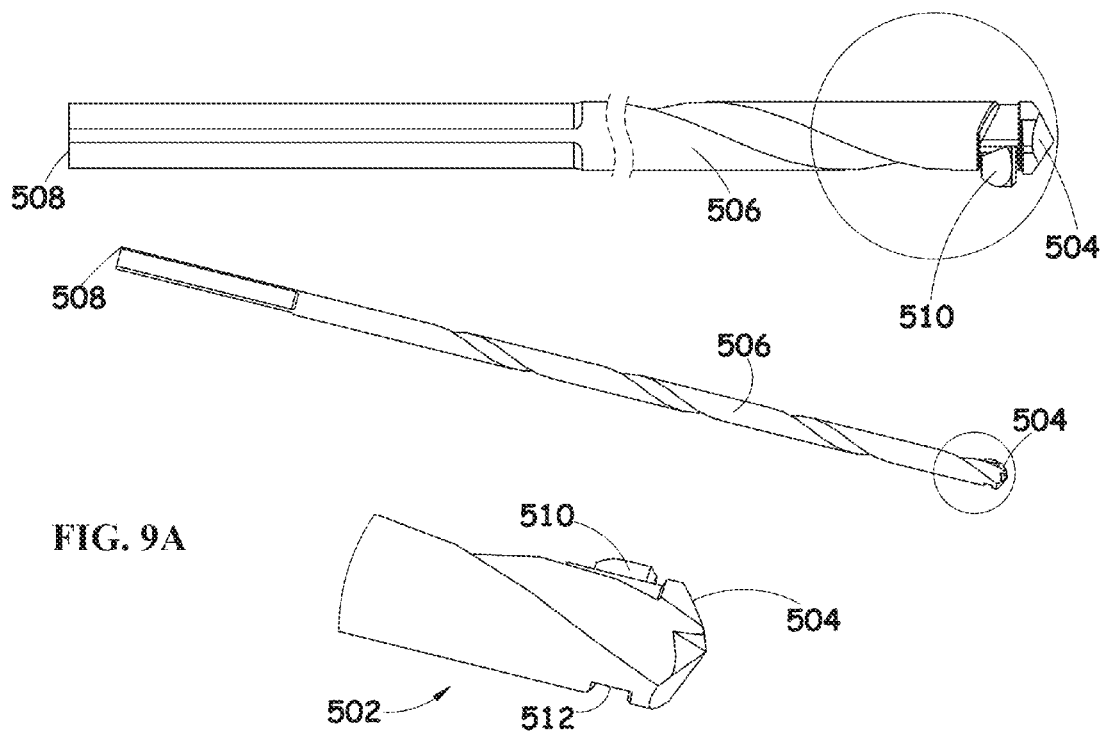
FIG. 9A is a pictorial view and an enlargement view of the bone material removal device of FIGS. 5A-6B in a closed configuration, according to some embodiments of the invention.

Reference is now made to FIGS. 9A-9C, showing the bone material removal device 500 in a closed configuration, a partially open configuration and an expanded open configuration respectively.

It is seen in FIG. 9A that the cutting tooth 510 slightly extends beyond the outer circumference of the shaft 506, when the cutting tooth 510 is in the closed configuration.

It is seen in FIG. 9B that the cutting tooth 510 extends further beyond the outer circumference of the shaft 506 as the cutting tooth partially opens.

It is further seen in FIG. 9C that the cutting tooth 510 maximally extends beyond the outer circumference of the shaft 506, when the cutting tooth 510 is in the open configuration.

Figure 10B:
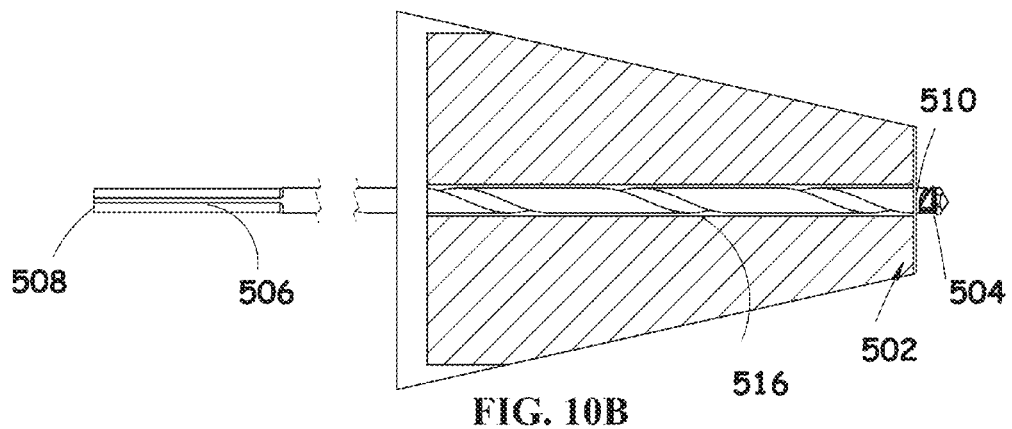
FIGS. 10A-10C are a pictorial view, two sectional views and an enlargement view of the bone material removal device of FIGS. 5A-6B in a closed configuration, shown within a bone portion after a bore of a first diameter was drilled through the bone portion, according to some embodiments of the invention.
Figure 10A:
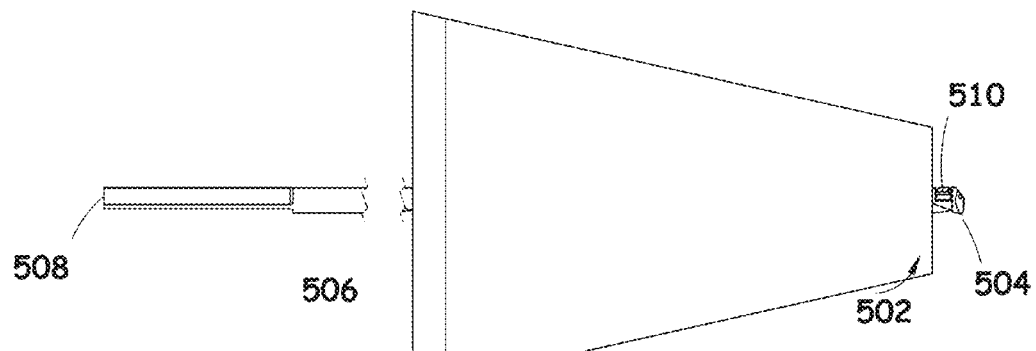
Figure 10C:
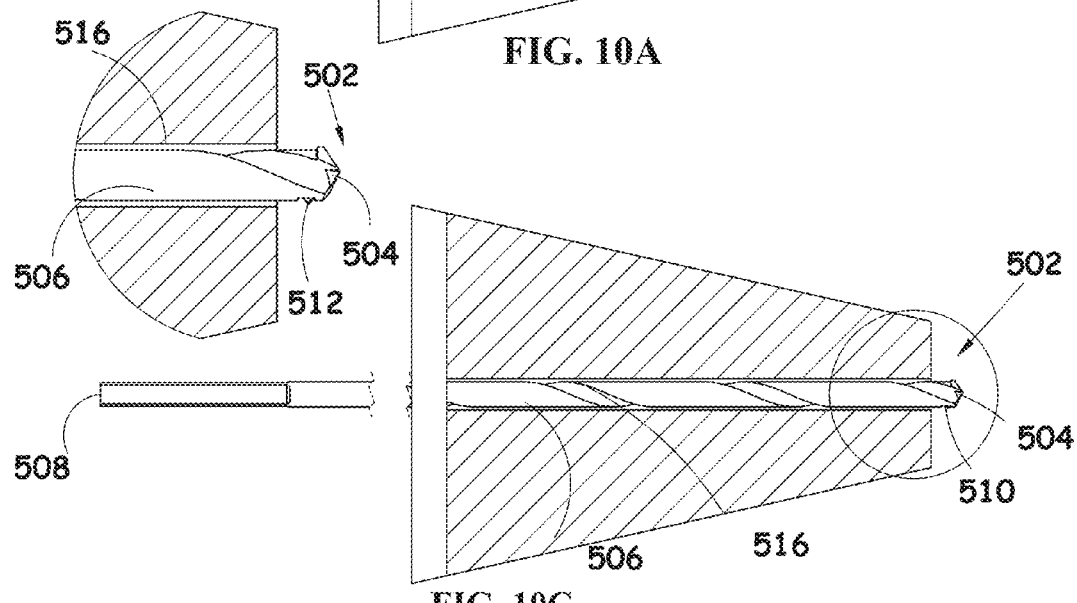

Reference is further made to FIGS. 10A-10C, showing the bone material removal device in a closed configuration, shown within a bone portion when a bore of a first diameter was drilled through the bone portion.

It is seen in FIGS. 10A-10C that the drill of the bone material removal device 500 is used in a closed configuration for providing a bore of a first diameter 516 within a bone portion by inserting the distal tip 504 into the bone portion and rotating the device 500, for example by connection to a drill, drilling through the entire bone portion until the expanding portion 502 extends out of the bone portion and the cutting tooth 510 is either positioned distally of the bone portion or abuts the bone portion.

The drill is rotated preferably in a clockwise direction, keeping the cutting tooth 510 in a closed configuration, such that the cutting tooth 510 slightly extends beyond the circumference of the shaft 506.

Figure 11B:
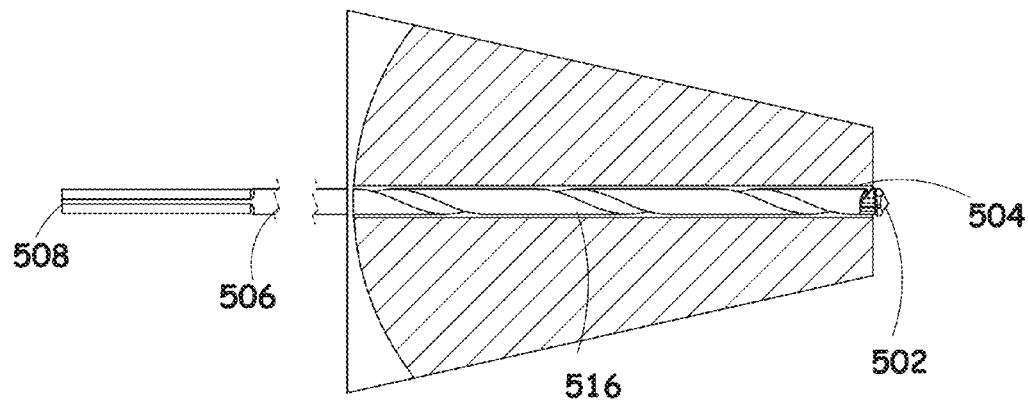
FIGS. 11A-11C are a pictorial view and two sectional views of the bone material removal device of FIGS. 5A-6B in an expanded configuration, shown within a bone portion after a bore of a first diameter was drilled through the bone portion, according to some embodiments of the invention.
Figure 11A:
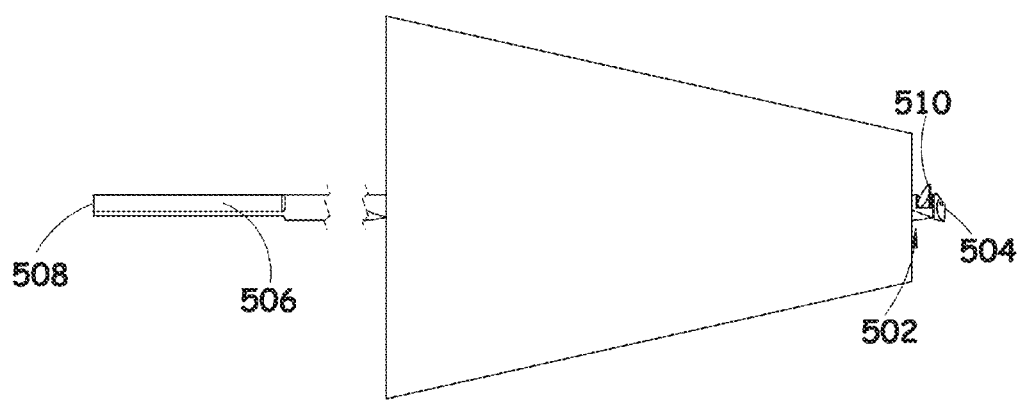
Figure 11C:
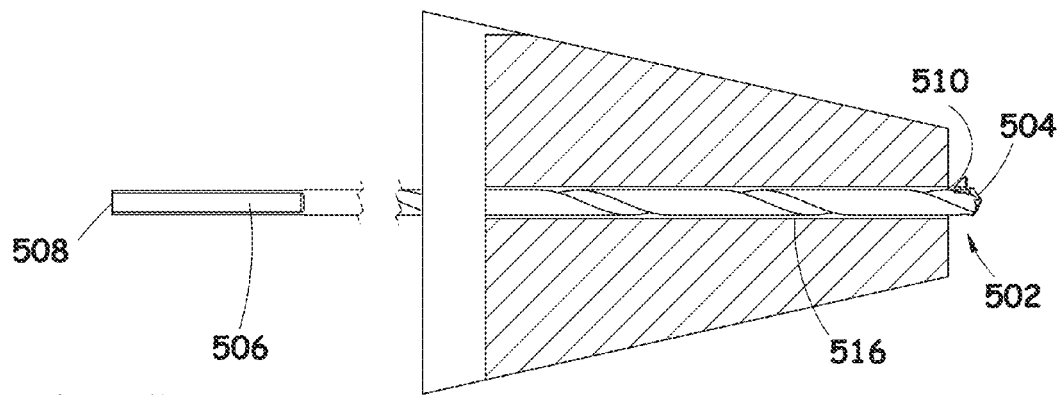

Reference is now made to FIGS. 11A-11C, showing the bone material removal device 500 in an expanded configuration, shown partially within a bone portion when a bore of a first diameter was drilled through the bone portion.

It is seen in FIGS. 11A-11C that the drill of the bone material removal device 500 is used in an expanded configuration for providing a bore of a second diameter 518, preferably greater than the first diameter, by reversing the rotation direction of the drill and drilling in an opposite axial direction through a portion of the bore of the first diameter to provide a widened bore portion.

It is appreciated that the frictional forces which appear between the cutting tooth 510 and the bone portion and centrifugal forces caused by reversing direction of rotation of the drill provide for the cutting tooth 510 to expand and assume an open configuration.

Figure 12A:
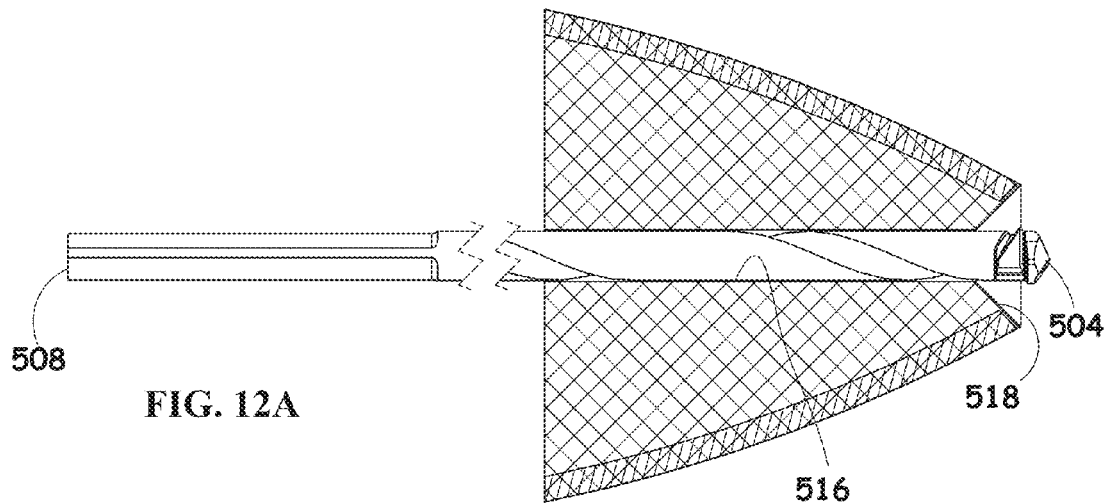
FIGS. 12A-12B are two sectional views of the bone material removal device of FIGS. 5A-6B in an expanded configuration, shown within a bone portion when a bore of a second diameter was drilled partially through the bone portion, according to some embodiments of the invention.
Figure 12B:
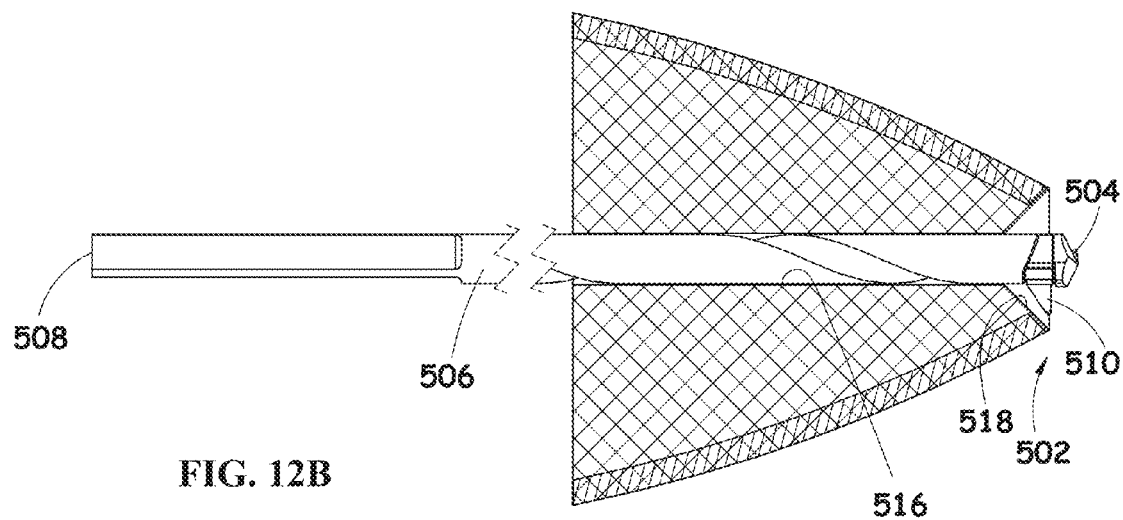

Reference is now made to FIGS. 12A-12B, showing the bone material removal device 500 in an expanded configuration, shown within a bone portion when a bore of a second diameter was drilled partially through the bone portion.

Following reversing of the rotation direction of the drill, the drill is pulled proximally back into the drilled bore of a first diameter 516 and due to the expanded configuration of the cutting tooth 510, a bore of a second diameter 518 is formed partially through the bone portion, along the bore of a first diameter 516, which was previously formed.

Figure 13A:
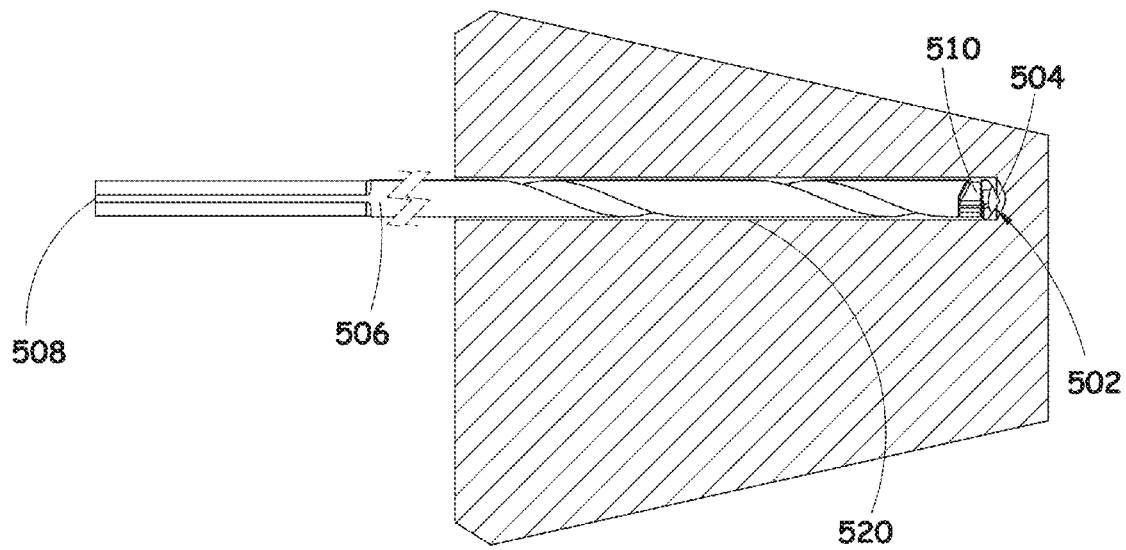
FIGS. 13A-13B are two sectional views of the bone material removal device of FIGS. 5A-6B shown within a bone portion, showing an additional method of use of the device, where a bore of a first diameter was drilled partially through the bone portion and the bone material removal device is shown in a closed configuration, according to some embodiments of the invention.
Figure 13B:
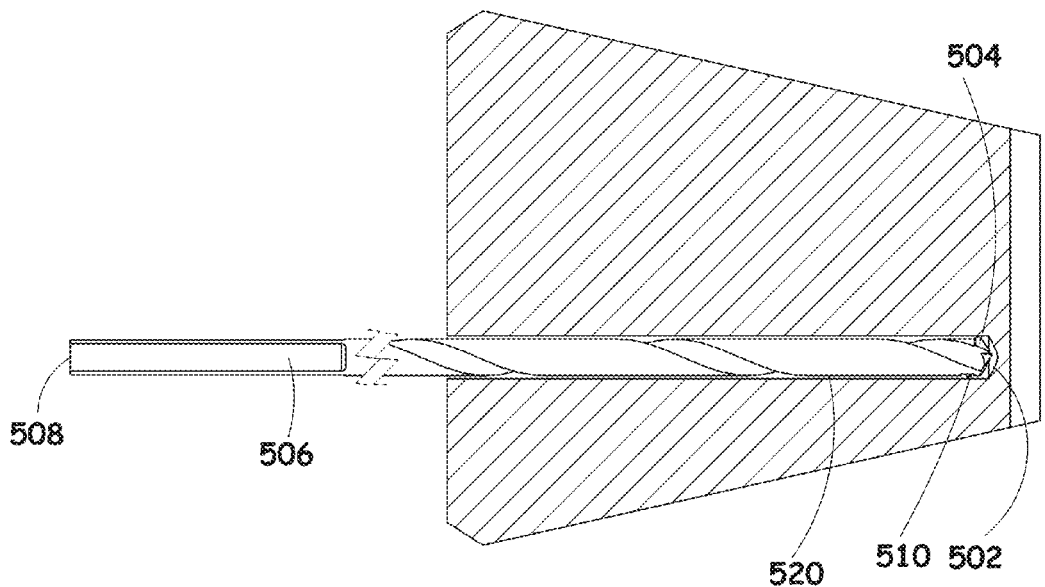

Reference is now made to FIGS. 13A-13B, showing the bone material removal device 500 shown within a bone portion, showing an additional method of use of the device, where a blind bore of a first diameter was drilled partially through the bone portion and the bone material removal device is shown in a closed configuration.

It is seen in FIGS. 13A-13B that the drill of the bone material removal device 500 is used in a closed configuration for providing a bore of a first diameter 516 within a bone portion by inserting the distal tip 504 into the bone portion and rotating the device 500, for example by connection to a drill, preferably drilling a blind bore of a first diameter 520, so that the distal tip 504 of the bone material removal device 500 is positioned within the bone portion and does not extend beyond the bone portion, such that the cutting tooth 510 also resides within the bone portion.

The drill is rotated preferably in a clockwise direction, keeping the cutting tooth 510 in a closed configuration, such that the cutting tooth 510 slightly extends beyond the circumference of the shaft 506.

Figure 14A:
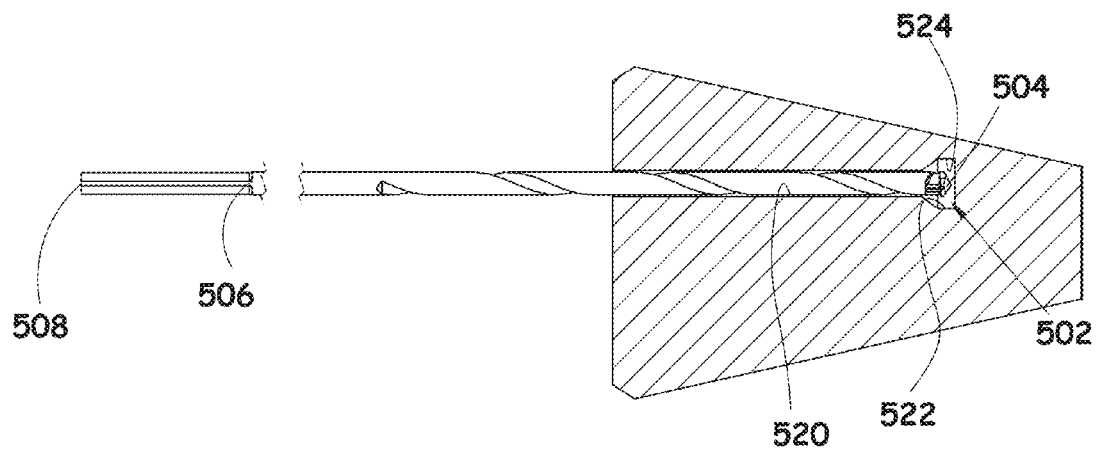
FIGS. 14A-14B are two sectional views of the bone material removal device of FIGS. 5A-6B shown within a bone portion, showing an additional method of use of the device, where a bore of a second diameter was drilled partially through the bone portion and the bone material removal device is shown in an expanded configuration, according to some embodiments of the invention.
Figure 14B:
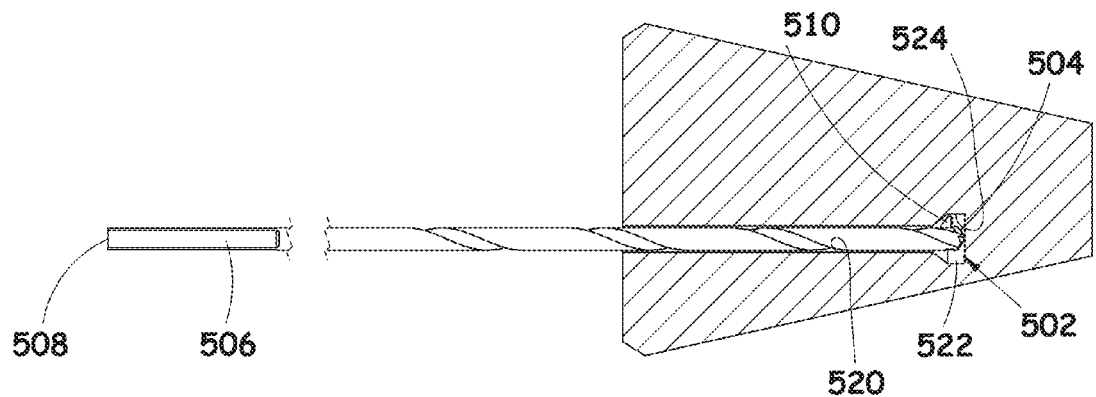

Reference is now made to FIGS. 14A-14B, showing the bone material removal device 500 within a bone portion, showing an additional method of use of the device, where a blind bore of a second diameter was drilled partially through the bone portion and the bone material removal device 500 is shown in an expanded configuration.

It is seen in FIGS. 14A-14B that the drill of the bone material removal device 500 is used in an open configuration for providing a blind bore of a second diameter 522, preferably greater than the first diameter, by reversing the rotation direction of the drill and drilling in an opposite axial direction through a portion of the bore of the first diameter to provide a widened bore portion, preferably forming an undercut 524 within the bone portion.

It is a particular feature of the present invention that the cutting tooth 510 which slightly extends beyond the circumference of the shaft 506, the extension may be in the range of 0.1 mm-0.5, in a closed configuration creates friction force with a portion of the bone once direction of rotation is reversed. The resulting friction force causes expansion of the cutting tooth 510 and provides for drilling a bore of second diameter 522, while assuming an open configuration.

Following reversing of the rotation direction of the drill, the drill is pulled proximally back into the drilled bore of a first diameter 520 and due to the expanded configuration of the cutting tooth 510, a bore of a second diameter 522 is formed partially through the bone portion, along the bore of a first diameter 520, which was previously formed.

It is a particular feature of the present invention that a blind undercut, consisting of a bore of a first diameter 520 and a bore of a second diameter 522, is formed by a single bone material removal device 500, without removing the device 500 from the bone.

It is appreciated that the described blind undercut may be used for positioning of an anchor within the bone.

In an exemplary embodiment of the present invention, the distal expandable portion 502 may be integrally formed with the longitudinal shaft 506 of the drill.

In accordance with another embodiment of the present invention, the distal expandable portion 502 is attachable to the longitudinal shaft 506 of the drill, preferably using a threadable connection. In accordance with this embodiment, the drill may be used as described above in order to form a variable diameter bore, consisting of a bore of a first diameter 520 and a bore of a second diameter 522 and then the longitudinal shaft 506 of the drill may be threadably disattached from the expandable distal portion 502, the expandable distal portion 502 preferably is fixedly positioned within the formed blind undercut and is used as an anchor.

Since after the bore of the second diameter 522 is formed, the cutting tooth 510 is positioned in an open expanded configuration, the distal expandable portion 502 is securely positioned within the bone portion and cannot be proximally removed, thus it provides for a safe anchor.

In accordance with another embodiment of the present invention, the length of the distal portion 502 is greater than the diameter of the bone material removal device 500 and the distal expandable portion 502 is attachable to the longitudinal shaft 506 of the drill by non-threadable connection. In accordance with some embodiments, the drill may be used as described above in order to form a variable diameter bore, consisting of a bore of a first diameter 520 and a bore of a second diameter 522 and then the longitudinal shaft 506 of the drill may be disattached from the expandable distal portion 502. The distal portion will then change orientation within the blind undercut, rotating approximately 90 degrees to its initial longitudinal orientation. Since the length of the expandable distal portion 502 is greater than the first diameter 520, the distal expandable portion 502 is securely positioned within the bone portion and cannot be proximally removed, thus it provides for a safe anchor.

It is appreciated that in accordance with an exemplary embodiment in which the distal portion is detachable from the longitudinal shaft 506 of the drill, the distal portion is formed of Titanium or any other biologically suitable material.

Reference is now made to FIGS. 15A-15B, which show two elevation views of a drill 600 of a bone removal device similar to the bone removal device shown in FIGS. 5A-5B, constructed according to yet another embodiment of the present invention.

The drill 600 includes a longitudinal shaft 606 having a proximal end 608, a distal tip 610 and a recess 612 for insertion of a cutting tooth therein. In some embodiments, distal tip 610 is a drill bit, optionally having a threaded portion.

It is noted that the drill is cannulated, including a longitudinal bore extending from the distal tip 610 to the proximal end 608 for flushing or removal of residual drilling materials.

Figure 16A:
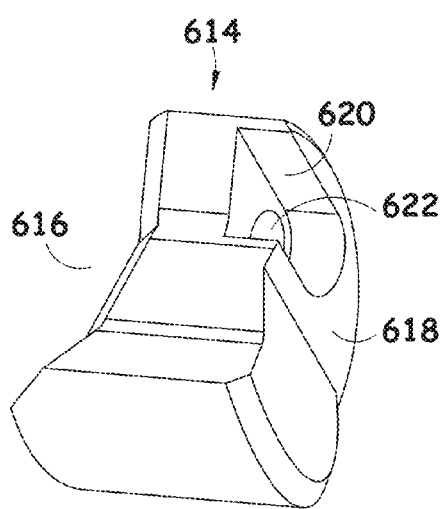
FIGS. 16A-16C are a pictorial view and two elevation views of a cover of the bone removal device, according to some embodiments of the invention.
Figure 16B:
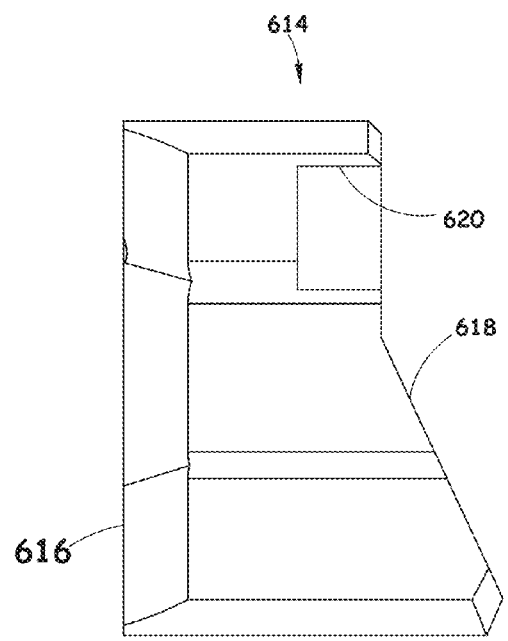
Figure 16C:
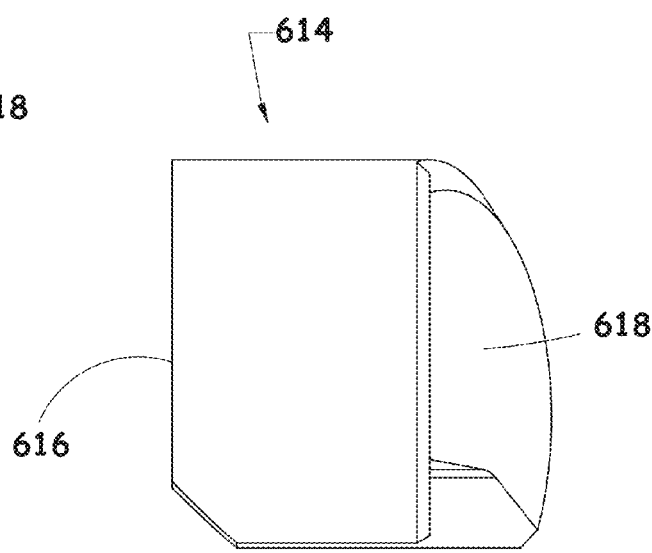
Figure 17D:
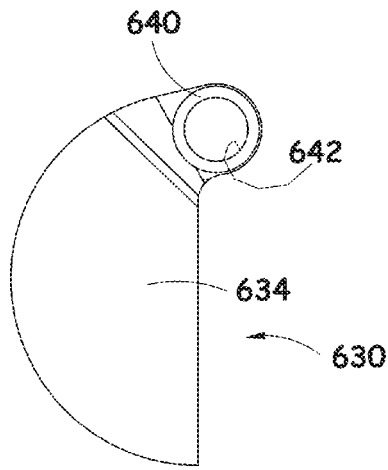
FIGS. 17A-17D are a pictorial view and three different elevation views of a cutting tooth of the bone removal device, according to some embodiments of the invention.
Figure 17C:
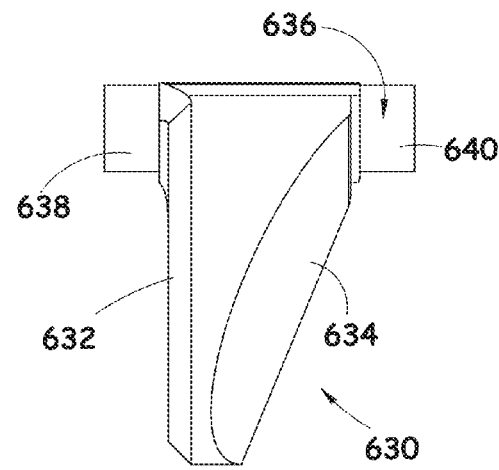
Figure 17A:
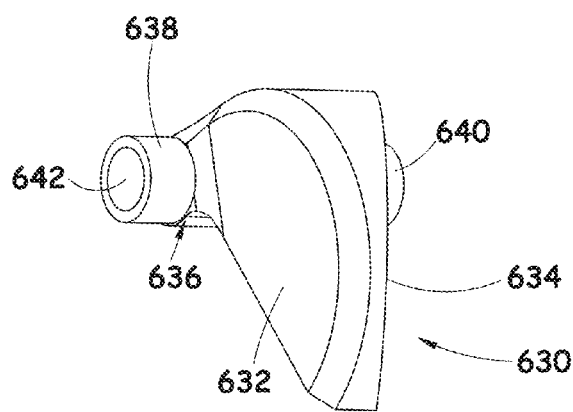
Figure 17B:
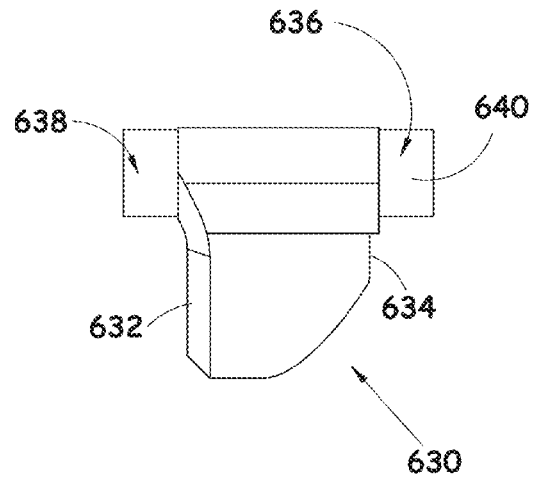

Reference is now made to FIGS. 16A-16C, which illustrate a cover 614 insertable into recess 612 of the drill 600 of the bone material removal device.

The cover 614 is shaped such that it outer dimensions preferably correspond to the circumference of the drill 600 of the bone removal material. The cover 614 has a proximal end 616 and a distal end 618. It is seen particularly in FIGS. 16A and 16B that a recess 620 is formed in the distal end 618 of the cover 614 for insertion of a hinge pin within, as shown and described further in detail. A longitudinally extending bore 622 is formed within recess 620.

Reference is now made to FIGS. 17A-17D, which illustrate an exemplary design of a cutting tooth 630 insertable into recess 612 of drill 600 of the bone material removal device.

The cutting tooth 630 has a proximal end 632 and a distal end 634 and a supporting member 636, which has a generally cylindrical proximal portion 638 extending proximally from the proximal end 632 and a generally cylindrical distal portion 640 extending distally from the distal end 634. A longitudinal bore 642 extends through the entire length of the supporting member 636.

Figure 18B:
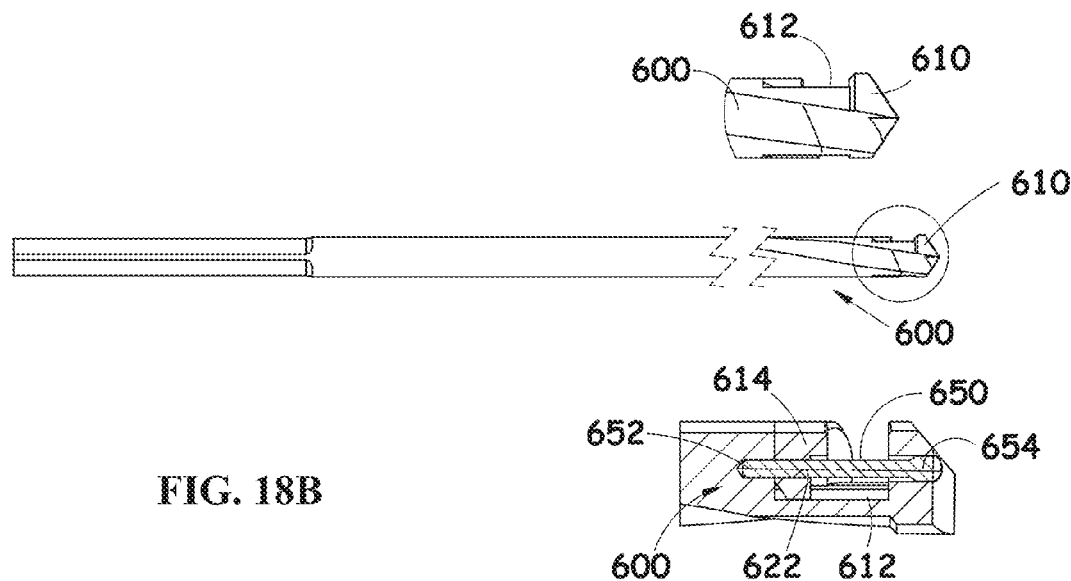
FIGS. 18A-18B are two elevation views and corresponding enlargements of a partial assembly of the bone removal device, showing the drill and the cover of the bone removal device.
Figure 18C:
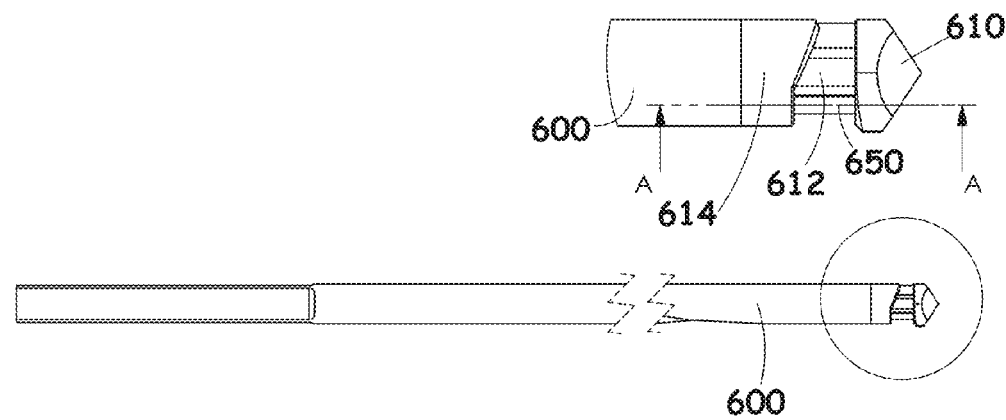
FIG. 18C is an elevation view, enlargement and a section view of a partial assembly of the bone removal device, showing the drill and cover of the bone removal device, according to some embodiments of the invention.
Figure 18A:
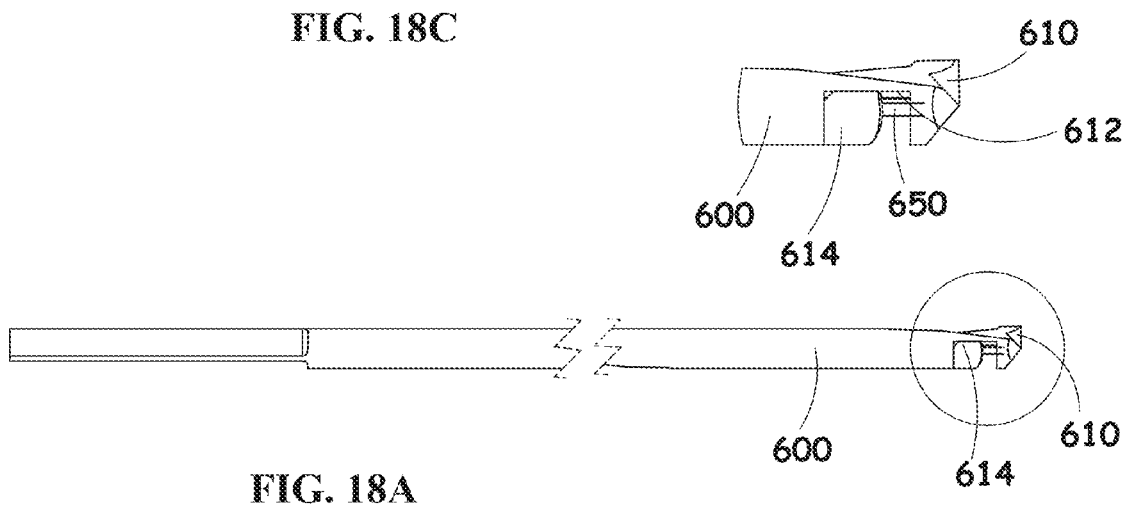

Reference is now made to FIGS. 18A-18C, which illustrate a partial assembly of the bone removal device, showing the drill 600 and the cover 614 of the bone removal device assembled using a hinge pin 650. It is particularly seen in the section view of FIG. 18C that the cover 614 is inserted into the recess 612 of the drill 600 and the hinge pin 650 has a proximal end 652 inserted into bore 622 of the cover 614 and a distal end 654 inserted into the bore formed within the drill 600.

It is appreciated that the length of hinge pin 650 is such that both the proximal end 652 and the distal end 654 of the hinge pin 650 extend substantially into the drill 600 and firmly held therewithin.

Reference is now made to FIGS. 19A-19C, which illustrate the bone material removal device in a closed configuration.

It is particularly seen in FIG. 19C that the cutting tooth 630 is inserted into the recess 612 of the drill 600 of the bone removal device using the hinge pin 650. It is seen that the proximal end 632 of the cutting tooth 630 engages the distal end 618 of the cover 614 and that the distal portion 638 of the supporting member 636 of the cutting tooth 630 is inserted into the recess 620 and the longitudinal bore 622 of the cover 614. The distal portion 640 of the supporting member 636 of the cutting tooth 630 is inserted into the longitudinal bore of the drill 600.

It is a particular feature of some embodiments of the present invention that the aforementioned assembly of drill 600 and cutting tooth 630 using a hinge pin 650 enables secure pivotable connection between the drill 600 and the cutting tooth 630. Due to insertion of the hinge pin 650 into the recess 620 formed in the cover 614 and the fact that the hinge pin 650 is firmly held at both of its ends within the drill 600, the cutting tooth 630 is securely held in the recess 612 of the drill 600 and cannot be removed therefrom.

It is a particular feature of the present invention that even in case that the hinge pin 650 is broken, the cutting tooth 630 is securely held attached to the drill 600 due to the supporting member 636, which is irreversibly inserted into the drill 600 at one end and into the cover 614 at the other end.

It is thus noted that the cutting tooth 630 is irremovably attached to the drill 600 by at least one of a hinge pin 650 or supporting member 636.

It is appreciated that increasing the length of the hinge pin 650 correspondingly increases the force that may be exerted on the drill without resulting in breaking of the hinge pin 650.

It is seen in FIGS. 19A-19C that the cutting tooth 630 slightly extends beyond the outer circumference of the shaft 606 when the cutting tooth 630 is in the closed configuration.

Figure 20C:
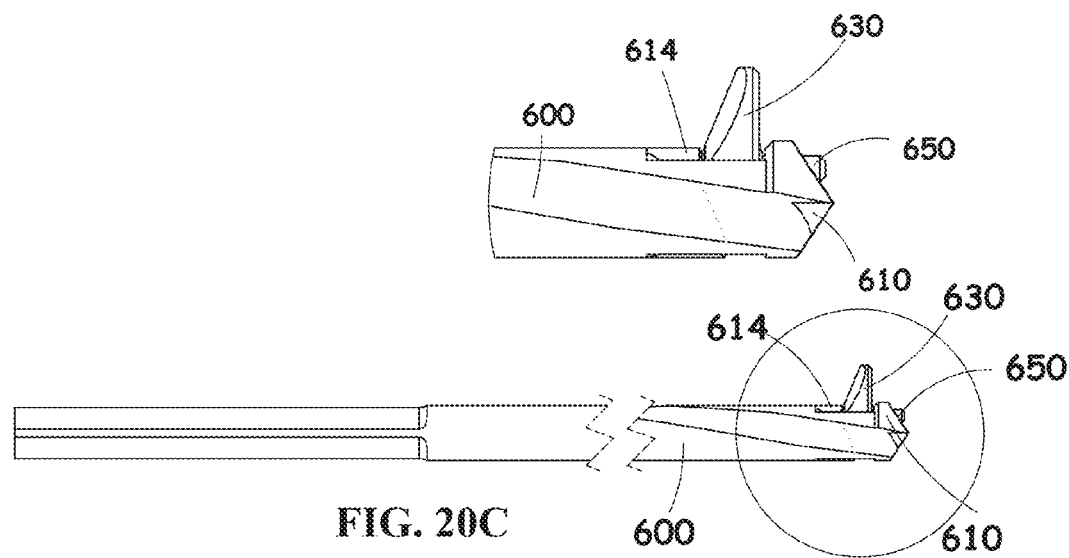
FIGS. 20A-20C are three different elevation views and corresponding enlargements of the assembled bone removal device, showing the expandable tip in an expanded configuration, according to some embodiments of the invention.
Figure 20B:
Figure 20A:
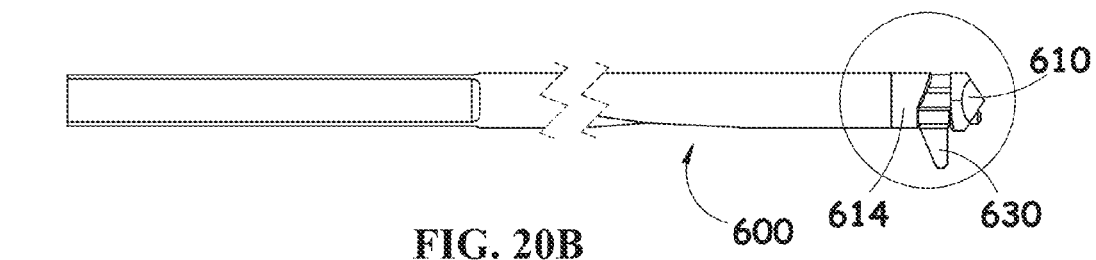

Reference is now made to FIGS. 20A-20C, which illustrate the bone material removal device in an expanded configuration.

The cutting tooth 630 is pivotable about the hinge pin 650. It is seen that in the open expanded configuration the cutting tooth 630 maximally extends beyond the outer circumference of the shaft 606.

The operation of the bone material removal device shown in FIGS. 15A-20C is similar to the operation of bone material device 500, which is shown in FIGS. 10A-14B.

Figure 21:
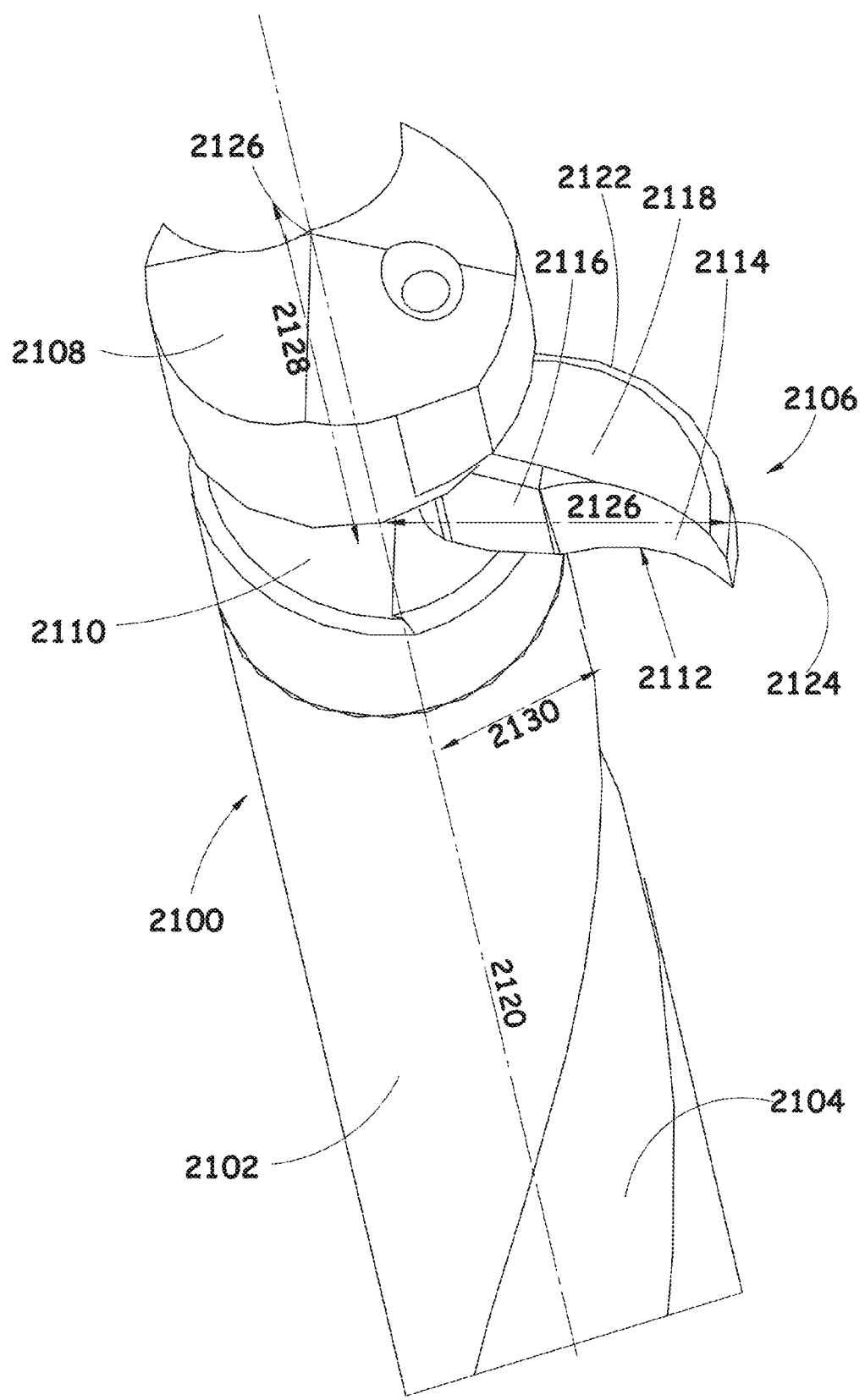
FIG. 21 is an exemplary bone material removal device comprising an extendible cutting tooth, according to some embodiments of the invention.

FIG. 21 shows an exemplary bone material removal device 2100, comprising an extendible cutting tooth 2106, according to some embodiments of the invention.

In some embodiments, device 2100 comprises a shaft 2102. Optionally, a head 2108 is configured at a distal end of the shaft.

In some embodiments, cutting tooth 2106 is at least partially received within a recess 2110 formed in shaft 2102, for example when the tooth is in a closed configuration.

In some embodiments, cutting tooth 2106 is pivotally connected to shaft 2102, for example by a hinge.

In some embodiments, the hinge (hidden in this figure) is positioned along a central, longitudinal axis 2120 of the shaft. Alternatively, the hinge is positioned offset from axis 2120, for example positioned at a distance ranging between, for example, 0.5-2 mm, such as 0.7 mm, 1.3 mm, 1.8 mm or intermediate, larger or smaller distances from axis 2120.

In some embodiments, for example as shown herein, cutting tooth 2106 comprises a cutting face 2112. In some embodiments, cutting face 2112 formed with a curvature on at least a portion of the cutting surface. For example, at least a portion of the surface, such as portion 2114, is concave. Additionally or alternatively, at least a portion of the surface such as portion 2116 is flat.

In some embodiments, planar portion 2116 is configured in proximity axis 2120, while curved portion 2114 is configured radially outwardly to planar portion 2116. In some embodiments, such as during closing of the tooth, planar portion 2116 is pushed against an inner wall of recess 2110 within shaft 2102. Optionally, planar portion 2116 resists over-closure of the tooth (e.g. the tooth entering deeper within recess 2110 when force is applied to a back wall 2122 of the tooth). A potential advantage of a planar portion 2116 may include increased wear resistance and/or reduced risk of breakage when the tooth is being pushed into recess 2110 against the shaft material, for example as compared to closure over an edge or a corner of a tooth.

In some embodiments, a top surface 2118 of tooth 2106, facing a distal direction towards head 2108, is flat. Optionally, top surface 2118 is configured to engage a bottom surface of head 2108 when the tooth is in a closed position, for example formed as a flat surface suitable to contact a bottom surface of head 2108 such that no gaps are formed between the surfaces.

In some embodiments, in an open configuration, a radially outward edge 2124 of tooth 2106 is located at a distance 2126 from axis 2120 of the shaft ranging between, for example, 1.1-1.5 times a radius 2130 of the shaft, for example a radius of a shaft portion configured directly below recess 2110. Optionally, the distance 2126 is selected, for example by a surgeon, to produce a bore of a desired diameter. In some cases, a graft is harvested, and the extent of the open tooth is selected such as to widen a bore to a diameter suitable for receiving the graft.

In some embodiments, shaft 2102 is cylindrical, for example as shown herein. Optionally, when inserted to a bone, shaft 2102 defines a generally cylindrical volume of rotation, producing a bore with a similar geometry. Alternatively, shaft 2102 comprises a different geometry, for example comprising a polygonal cross section, such as hexagonal or octagonal cross section. Optionally, a volume or rotation defined by a shaft with a polygonal cross section is cylindrical as well.

In some embodiments, device 2100 is a drill bit, such as a twist-type drill bit. In some embodiments, shaft 2102 of the device is formed with one or more flutes 2104. Optionally, the twist rate of flute 2104 is selected to provide a certain bone chip removal rate.

In some embodiments, head 2108 comprises tapering distal end, optionally formed with a pointed tip 2126.

In some embodiments, tooth 2106 is located a distance from tip 2126 in a proximal direction, such as a distance 2128 from tip 2124 ranging between, for example, 4-7 mm, 3-9 mm, 2-5 mm or intermediate, larger or smaller ranges. Optionally, distance 2128 is selected, one the one hand, to be close enough to distal dip 2126 such as to reduce damage to tissue configured beyond the bone, and, on the other hand, to be spaced enough from distal tip 2126 so that it does not interfere with a drilling function of the tip and/or does not affect the strength of the distal portion.

In some embodiments, a proximal end of shaft 2102 (not shown in this figure) is configured to engage a drill, for example formed with a shank.

Various embodiments of bone material removal devices may include various numbers of cutting teeth, for example 2, 3, 4, 5, 8, 10 or intermediate, larger or smaller numbers of cutting teeth. Optionally, the plurality of cutting teeth are distributed circumferentially around the shaft. Optionally, the plurality of cutting teeth are positioned at various locations along longitudinal axis 2120.

Figures 22A, 22B:
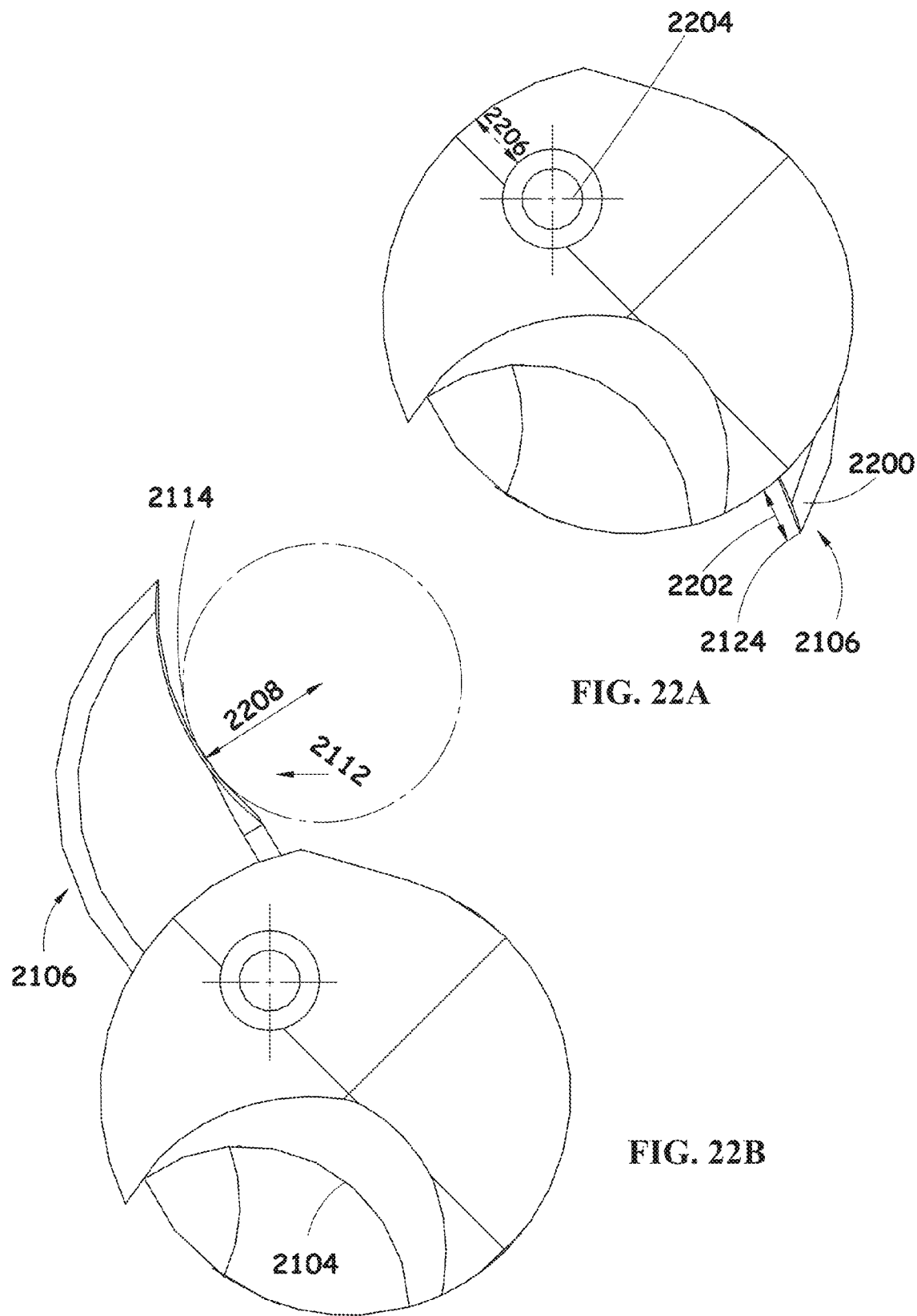
FIGS. 22A-B are front views of a device comprising a cutting tooth for bone removal, showing a closed configuration of the cutting tooth (A) and an open configuration of the cutting tooth (B), according to some embodiments of the invention.

FIGS. 22A-B are front views of a device comprising a cutting tooth for bone removal, showing a closed configuration of the cutting tooth (A) and an open configuration of the cutting tooth (B), according to some embodiments of the invention.

Referring to FIG. 22A, showing tooth 2106 in a closed configuration, in some embodiments, at least a portion 2200 of tooth 2106 extends beyond the shaft, for example extending to a distance 2202 from a periphery of shaft the shaft ranging between, for example, 0.1-0.4 mm, such as 0.2 mm, 0.3 mm, or intermediate, larger or smaller distances. Optionally, the protruding portion 2200 of tooth 2106 increases a diameter of a bore drilled by the device, for example increasing a diameter of the bore by 0.5%, 2%, 5%, 10% or intermediate, larger or smaller percentages in comparison to a diameter which would have been formed by the shaft without the protruding portion 2200 of the tooth. For example, if a diameter of the shaft is, for example, 4.5 mm, a diameter of a bore formed by the device with a protruding portion of a cutting tooth (when the tooth is in a closed configuration) may range between, for example, 4.6-5 mm.

In some embodiments, hinge 2204 (as this figure shows a front view of the device, 2204 indicates a location of the hinge) is positioned away from a periphery of the shaft, for example positioned at a distance 2206 ranging between 0.15-0.4 mm, such as 0.2 mm, 0.3 mm, 0.35 mm or intermediate, larger or smaller distances. A potential advantage of a hinge that is located away from a periphery of the shaft may include reducing the risk of damage, such as breakage, to the hinge.

In some embodiments, radially outward edge 2124 of protruding portion 2200 extends parallel to an axis defined by hinge 2204 (extending in a proximal-distal direction). Alternatively, edge 2124 is slanted, and configured at an angle with respect to an axis defined by hinge 2204.

FIG. 22B, shows tooth 2106 in an open configuration, according to some embodiments of the invention. In some embodiments, a radius of curvature 2208 of curved portion 2114, for example formed with a concave surface, ranges between, for example, 1.5 mm-4 mm.

In some embodiments, tooth 2106 is positioned with respect to shaft 2102 in a way that the concavity of cutting face 2112 faces an opposite direction from flute 2104, for example to provide an additional removal track for the removed bone material. Optionally, the concavity and the flute are diametrically opposed.

In some embodiments, tooth 2106 is formed of a rigid material, such as nitinol, stainless steel, platinum, other metals, polymers such as PEEK, and/or other rigid materials. Optionally, the tooth is formed of a material that is more rigid then bone tissue, so that it does not break and/or deform when engaging the bone.

In some embodiments, the device is rotated at a rate ranging between, for example, 0.01-1000 rpm, such as 5 rpm, 70 rpm, 250 rpm, 700 rpm, or intermediate, higher or lower rates. In some embodiments, the device is manually operated. Additionally or alternatively, the device is coupled, for example on a proximal end of the shaft, to a drill such as a surgical drill.

In some embodiments, a rigidity of the tooth is selected according to the rotation rate, for example the tooth is selected to be more elastic to withstand higher rotation rates and to reduce damage such as chipping to the tooth. Respectively, a more rigid tooth can be used with lower rotation rates.

In some embodiments, a rigidity of the tooth is selected according to the tissue in which the bore is drilled. In an example, for drilling in a tibia body portion, a tooth formed of titanium may be used. Optionally, rotational speed of 1000 rpm is applied. In another example, for drilling in a distal and/or proximal ends of the tibia, such as in the tibial plateau, the selected tooth may be formed of stainless steel (PH174), which is harder than titanium, and the rotational speed may be lower, for example 500 rpm.

Figure 23:
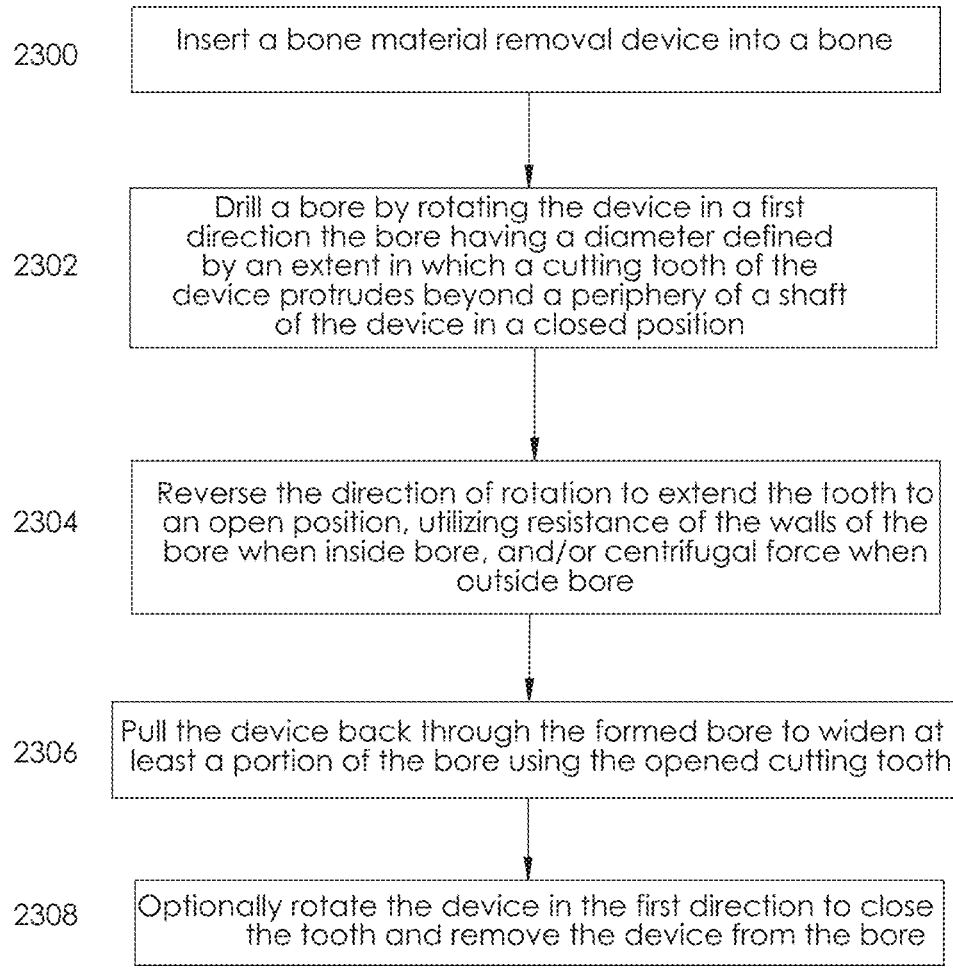
FIG. 23 is a flowchart of a method for drilling a bore, and widening at least a portion of the bore using a bone material removal device comprising a cutting tooth, according to some embodiments of the invention.

FIG. 23 is a flowchart of a method for drilling a bore, and widening at least a portion of the bore, according to some embodiments of the invention.

In some embodiments, a bone material removal device is inserted, such as by drilling, into a bone (2300). In some embodiments, inserting comprises rotating the device to form the bore (2302). In some embodiments, a cutting tooth of the device extends beyond a periphery of a shaft of the device, forming a bore with a diameter that is defined by the radial extent of the cutting tooth in a closed position.

In some embodiments, the device is inserted into the bone until exiting a face of the bone different than the entering face. Optionally, the device is advanced until at least the cutting tooth exits a distal opening of the bore. Alternatively, the device is advanced until other portions along the length of the device exit a distal opening of the bore.

Alternatively, in some embodiments, the device is advanced only a certain distance within the bone, and does not form a distal opening to the bore.

In some embodiments, for example once a required depth of the bore is obtained, the device is rotated in an opposite direction to the rotation direction used for insertion of the device (2304). In some embodiments, for example if the cutting tooth is within the bore, the protruding portion of the tooth is pushed against the walls of the bore. Optionally, as rotation continues, the resisting force applied by the walls of the bore on the protruding portion of the tooth increases, until the tooth is forced to rotate into an open configuration. Additionally or alternatively, rotation of the device in an opposite direction to the drilling direction causes opening of the tooth, for example due to centrifugal force. In some embodiments, rotation-based opening is performed when the tooth has been advanced passed the bone, and was positioned in a lumen which imposes less resistance to opening of the tooth, such as in comparison to the resistance imposed by the walls of the bore.

In some embodiments, the device comprising the opened tooth is pulled back in a proximal direction (2306), to widen at least a portion of the formed bore. Optionally, the device is rotated in a direction opposite to the initial drilling direction to keep the tooth in an open position. In some embodiments, the opened tooth cuts bone tissue surrounding the initial walls of the bore, thereby increasing a diameter of the bore.

In some embodiments, only a portion of the bore is widened. Optionally, the device is rotated once again in the first, initial drilling rotation to cause the tooth to close. Optionally, once the tooth is closed, the device is removed from the bore, such as through a proximal opening of the bore. Alternatively, the device is pulled along a complete length of the bore with the tooth in an open configuration, to widen the bore along its length.

Figure 24A:
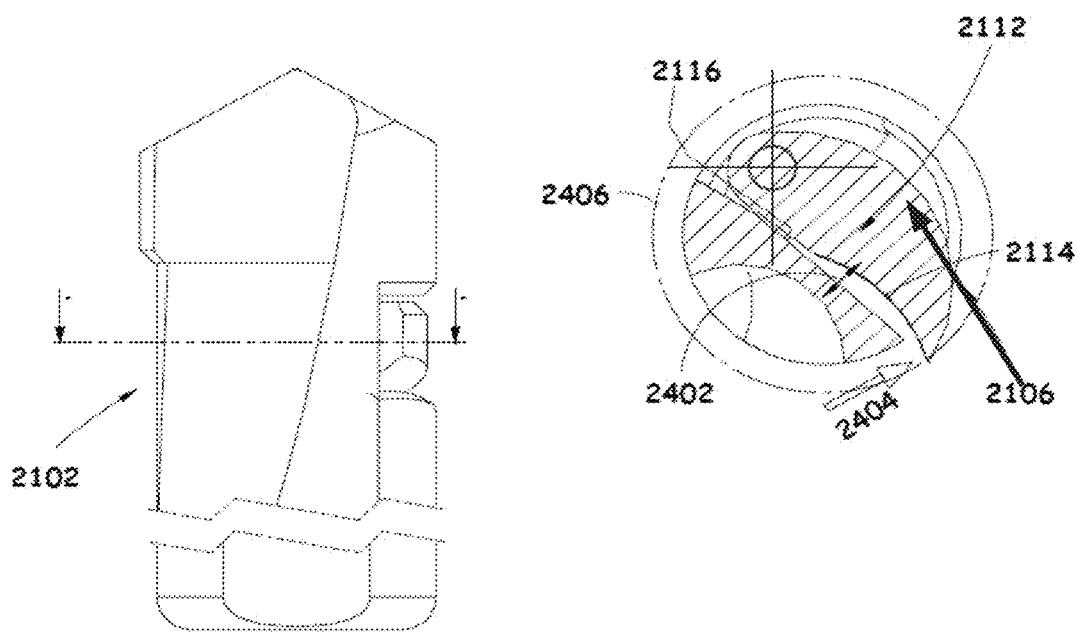
FIGS. 24A-B are cross sections of a shaft of a bone removal device showing an extendible cutting tooth, according to some embodiments of the invention.
Figure 24B:
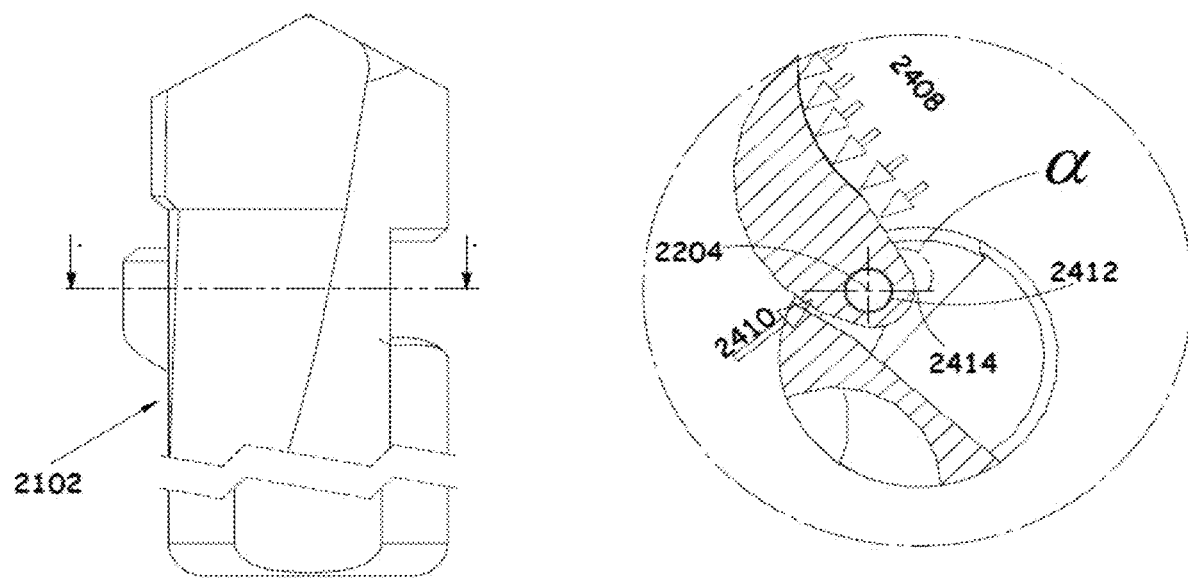

FIGS. 24A-B are cross sections of shaft 2102 at the cutting tooth 2106, according to some embodiments of the invention.

In some embodiments, for example as shown in FIG. 24A, cutting face 2112 leans against shaft wall 2400 when the tooth is in a closed position. Optionally, flat portion 2116 of the cutting face fully contacts shaft wall 2400, while concave portion 2114 defines a gap 2402 between the shaft wall 2400 and the cutting face. In some embodiments, gap 2402 ranges between, for example, 0.25-0.7 mm, such as 0.3 mm, 0.45 mm, 0.6 mm or intermediate, larger or smaller distances.

In some embodiments, for example when the device is rotated in an opposite direction to the drilling direction to open the tooth, force 2404, applied by walls of the formed bore 2406, acts on protruding portion 2200. Optionally, friction is created between edge 2124 of the cutting tooth and bore walls 2406. In some cases, force 2404 increases as the rotation continues, until causing tooth 2106 to spin open.

In some embodiments, for example as shown in FIG. 24B, various forces may act on open tooth 2106 during widening of the bore. In some cases, force 2408 is applied onto cutting face 2112 due to resistance of the bone tissue which the tooth cuts through. Optionally, the curvature of cutting face 2112 is configured to distribute force 2408 along cutting face 2112. Optionally, the arcuate configuration of concave portion 2114 spreads force 2408 over a larger surface area, for example as compared to a flat surface, reducing the magnitude of the force acting on each point along cutting face 2112.

In some embodiments, a force 2410 is applied by shaft wall 2400 onto back wall 2122. Optionally, force 2410 limits movement of tooth 2106, for example preventing tooth 2106 from over-opening.

In some embodiments, tooth 2106 is coupled to hinge 2204 in a way that enables tooth 2106 to rotate freely on hinge. In some embodiments, tooth 2106 comprises a recess 2412 to be threaded onto a rod of hinge 2204. Optionally, recess 2412 is shaped and/or sized to freely rotate on the rod hinge.

Alternatively, in some embodiments, hinge 2204 is configured to limit movement such as rotational movement of the tooth and/or axial movement (lengthwise movement) of the tooth, for example by comprising one or more projections which lock into respective recess in the shaft body for limiting movement of the tooth.

In some embodiments, hinge 2204 comprises an elastic element such as a spring. Optionally, the spring is used to actuate opening of the tooth.

In some embodiments, an opening angle α of tooth 2106, measured for example between flat surface 2116 of the tooth and horizontal axis 2414 extending through a center of hinge 2204 and indicating the location of the hinge, ranges between, 0-130 degrees, such as 60 degrees, 90 degrees, 120 degrees or intermediate, larger or smaller angles.

Figure 25:
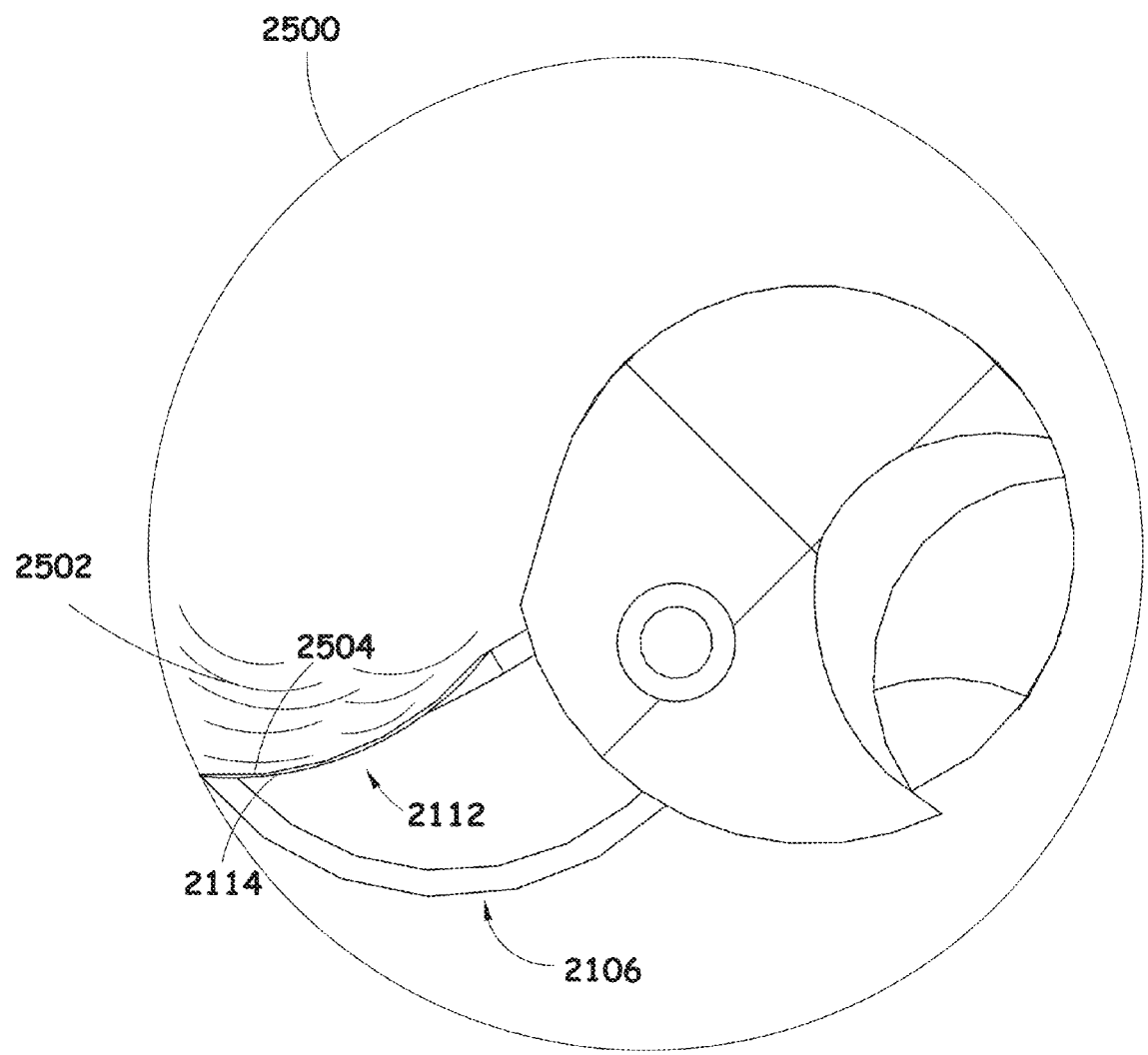
FIG. 25 is a front view of a bone removal device shown within a bore formed in the bone, according to some embodiments of the invention.
Figure 26A:
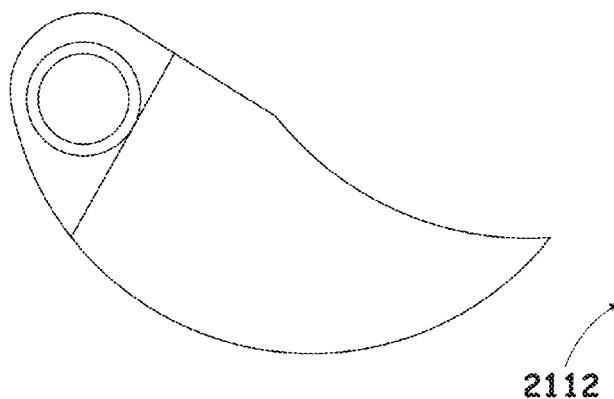
FIGS. 26A-E show a cutting tooth from various directions, according to some embodiments of the invention.
Figure 26B:
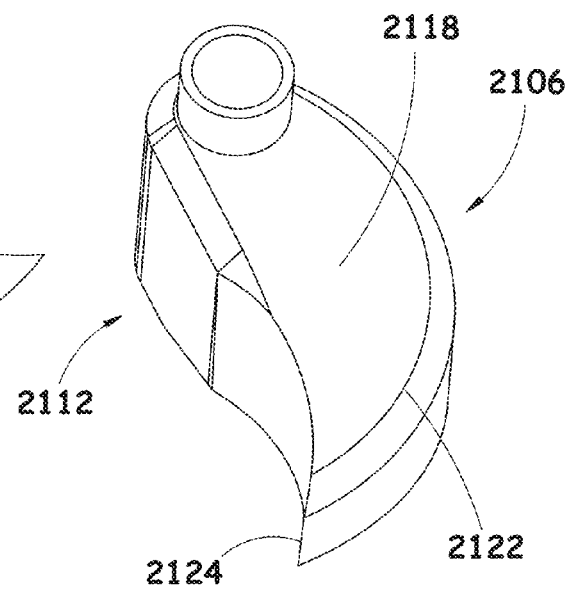
Figure 26C:
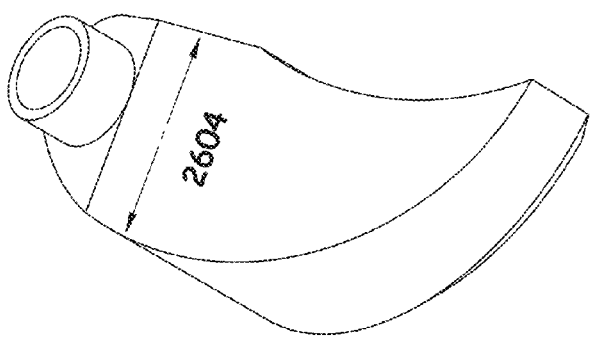
Figures 26D, 26E:
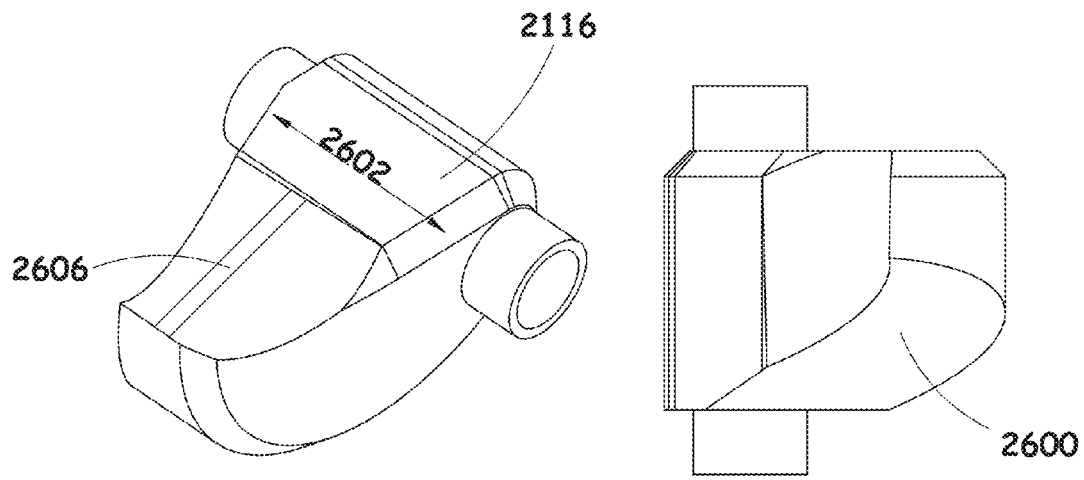

FIG. 25 is a front view of a bone removal device shown within a bore formed in the bone, according to some embodiments of the invention.

As shown in this figure, tooth 2106 is in an open configuration, effective to widen bore 2500. In some embodiments, cutting face 2112 is shaped to allow removal of the removed bone material 2502, for example including removed bone chips and/or dust. In some cases, for example when the device is used in a laparoscopic surgery, the bore is produced and/or widened in a fluidic environment, and the removed bone material is not formed as solid bone chips, but rather as fluid or paste. Optionally, the removed bone material is removed through the concavity of the cutting face. A function of the concavity of the cutting face 2112 can be compared to the function of a flute on a drill.

In some embodiments, the removed bone material 2502 which is formed during widening of the bore flows in various directions, for example flowing in a proximal direction, a distal direction, and/or radially outward direction towards the walls of bore 2500. In some embodiments, the removed bone material 2502 exits through a proximal opening and/or a distal opening of the bore. In some embodiments, during operation, at least some removed bone material may accumulate at a central area 2504 of concave portion 2114. Optionally, the bone material then flows in the proximal and/or distal direction passed the top and/or bottom surfaces of the tooth, "freeing" the tooth from the material temporarily, for example until the device is further rotated and new bone material is cut by the tooth 2106.

In some embodiments, when forming a bore, a system suitable for evacuating the removed bone material may be used, to clear the bore.

FIGS. 26A-E show a cutting tooth 2106 from various directions, according to some embodiments of the invention.

In some embodiments, a top surface 2118 of the tooth is flat. Alternatively, top surface 2118 is formed with a curvature.

In some embodiments, back wall 2122 is arc-shaped. Optionally, back wall 2122 is shaped and/or sized to flush with the shaft of the device when the tooth is closed.

In some embodiments, bottom surface 2600 of the tooth is formed with a curvature. Optionally, bottom surface 2600 is an inclined surface. Alternatively, bottom surface 2600 is flat.

In some embodiments, a height 2602 of tooth 2106, for example measured between the top and bottom surfaces along flat portion 2116, ranges between, for example, 2 mm-3 mm, 1 mm-4 mm, 2-6 mm, or intermediate, larger or smaller heights. Optionally, height 2602 varies along the radial axis of the tooth, for example it may decrease towards radially outwards edge 2124 which is farthest away from the shaft when the tooth is an open configuration. A potential advantage of a varying height of a tooth, which decreases in the direction of the outer walls of the bore, may include gradual application of force on the bone tissue that is being cut, which may facilitate removal of bone material.

In some embodiments, a width 2604 of tooth 2106, for example measured between back wall 2122 and cutting face 2112 at flat portion 2116, ranges between, for example, 1.5-3 mm, such as 1.7 mm, 2 mm, 2.5 mm or intermediate, larger or smaller widths.

In some embodiments, tooth 2106 comprises one or more slots or channels such as channel 2606 through which bone material can be removed. Optionally, the channel extends along cutting face 2112, for example extending in a radially outward direction to define a path towards the walls of the bore, and/or in a different direction, such as along the height of tooth 2106, to define a path for removing material in the proximal and/or distal directions of the bore.

In some embodiments, tooth 2106 is detachable from the bone removal device.

In some embodiments, a kit comprising a bone removal device and a plurality of different shapes and/or sizes of teeth is provided, and a tooth is selected according to the type and/or size and/or shape of the bone, and/or a shape and/or size of the bore to be formed in the bone. In some embodiments, a unit comprising a cutting tooth is provided, for example constructed as a shaft segment which can be assembled and/or detached from the rest of the shaft of the device. Optionally, the unit includes a distal head of the device in addition to the tooth.

Figure 27:
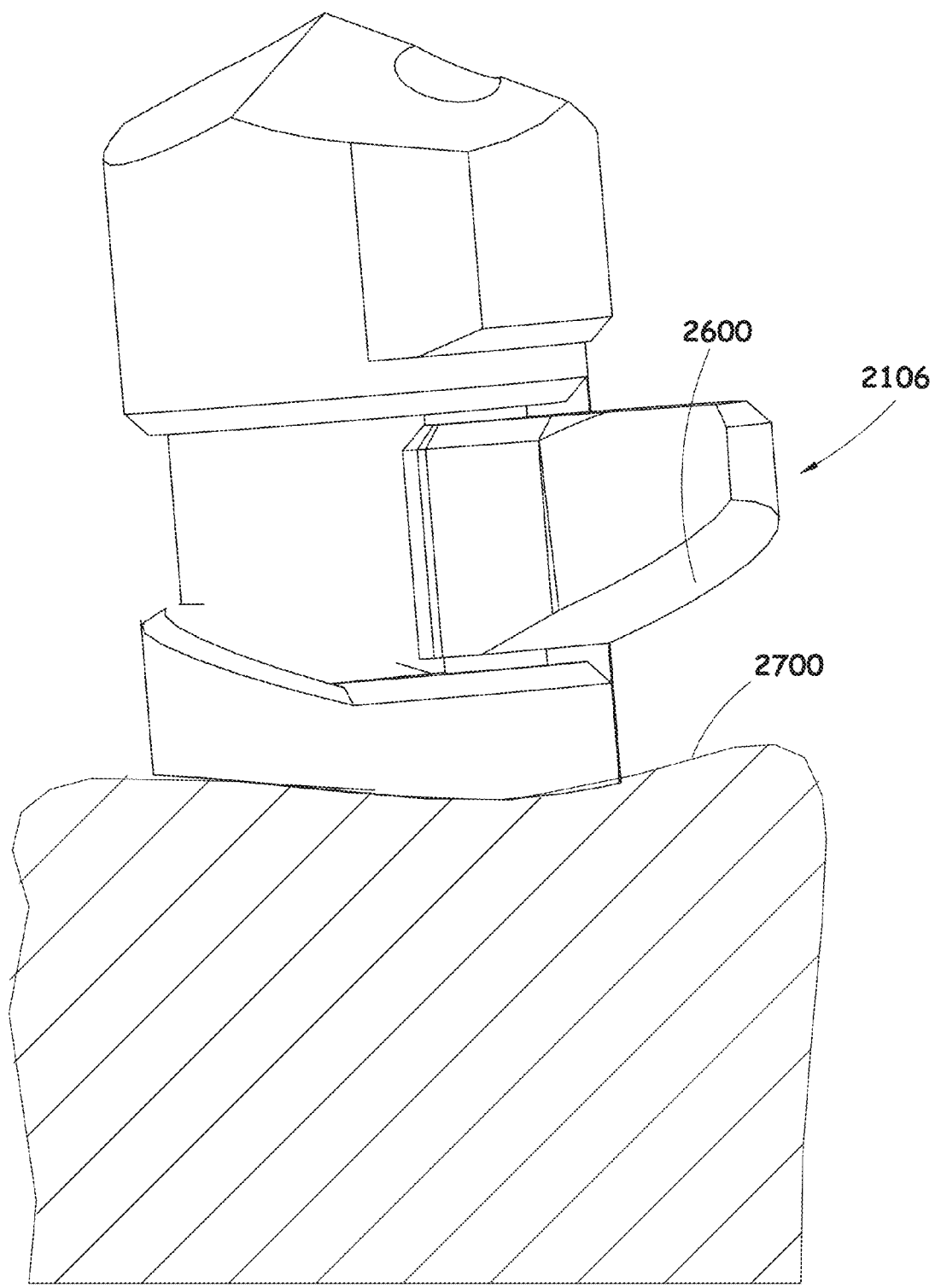
FIG. 27 illustrates a cutting tooth of a bone material removal device positioned against a bone surface, for example before widening a formed bore in the bone, according to some embodiments of the invention.

FIG. 27 illustrates a cutting tooth 2106 of a bone material removal device positioned against a bone surface 2700, for example before back-drilling to widen a formed bore in the bone, according to some embodiments of the invention. As described herein, bottom surface 2600 is formed with a curvature and/or inclination, suitable to engage a non-planar geometry of the bone surface 2700.

Figure 28:
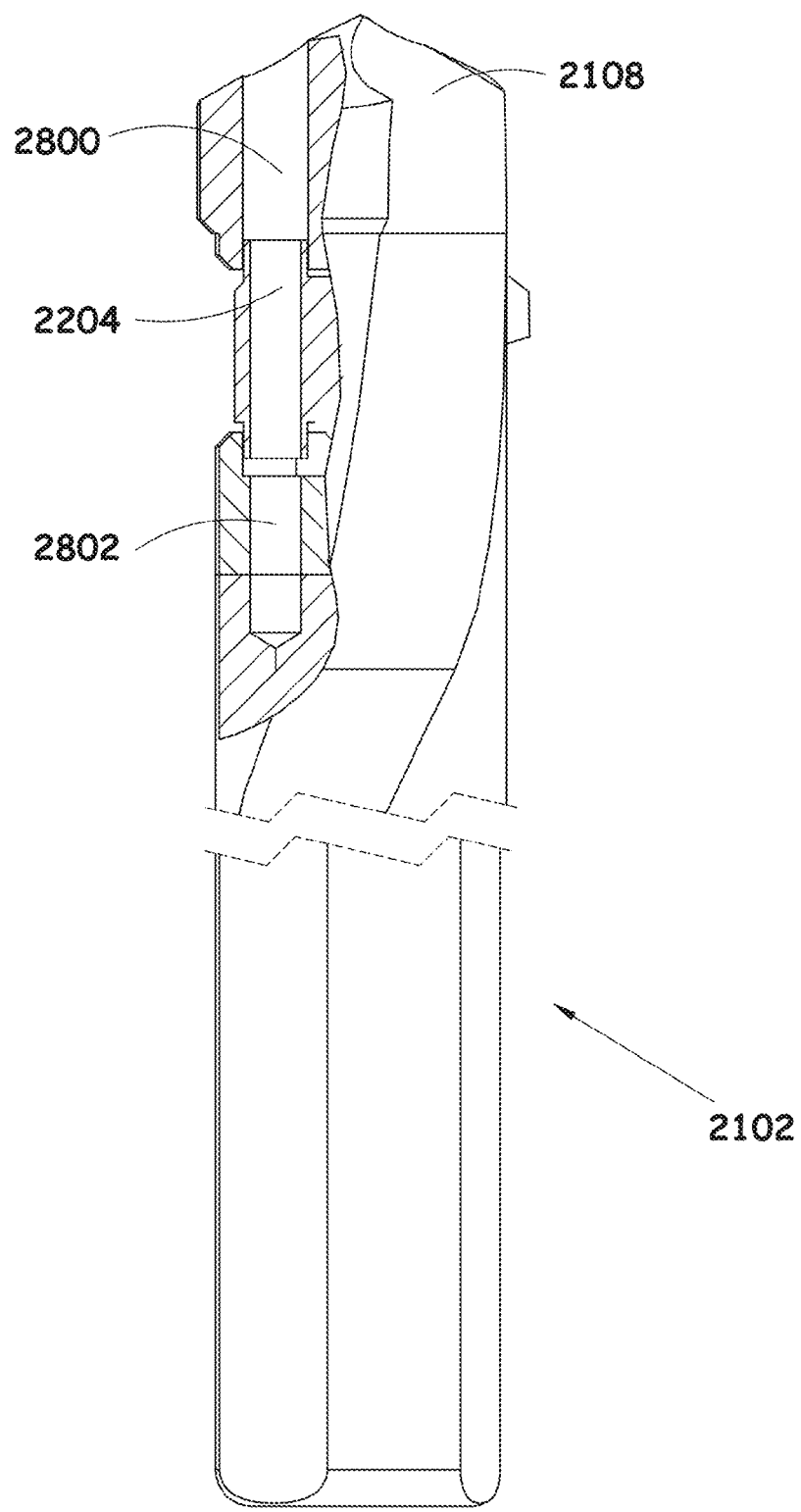
FIG. 28 is an illustration of shaft of a bone material removal device comprising a hinge, according to some embodiments of the invention.

FIG. 28 is an illustration of shaft 2102 of a bone material removal device comprising a hinge 2204, according to some embodiments of the invention.

In some embodiments, for example as shown in an exposed portion of the shaft, hinge 2204 comprises a rod formed with a distal 2800 extension and/or a proximal extension 2802. In some embodiments, distal extension 2800 is received within a recess in head 2108. In some embodiments, proximal extension 2802 is received within a recess in the inner body of shaft 2102. Optionally, extensions 2800 and 2802 secure the hinge in place, reducing a risk of disengagement of the hinge and thereby of the cutting tooth. Optionally, a length of an extension such as 2802 is, for example, at least 3 mm, at least 5 mm, at least 6 mm or intermediate larger or smaller lengths. Optionally, length 2800 ranges between, for example, 4-7 mm, 3-9 mm, 2-5 mm or intermediate, larger or smaller ranges. In some embodiments, distal extension 2800 extends to a distal end of head 2108, but does not surpass the distal end of the head.

Figure 29A:
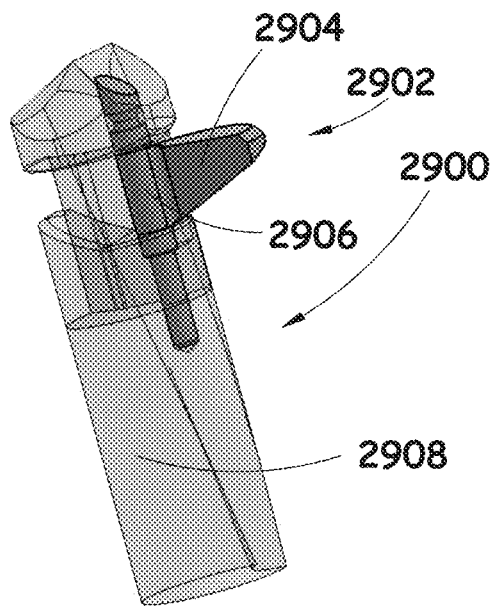
FIGS. 29A-C show an exemplary bone material removal device comprising a cutting tooth formed with a flat cutting face, according to some embodiments of the invention.
Figure 29B:
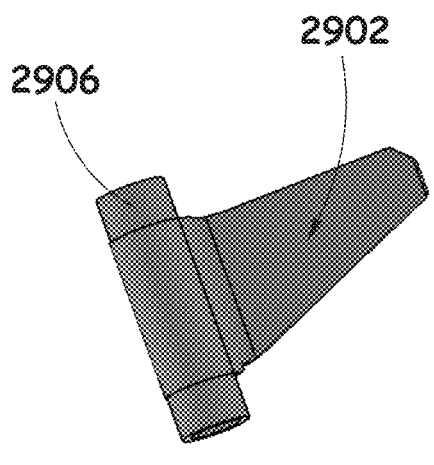
Figure 29C:
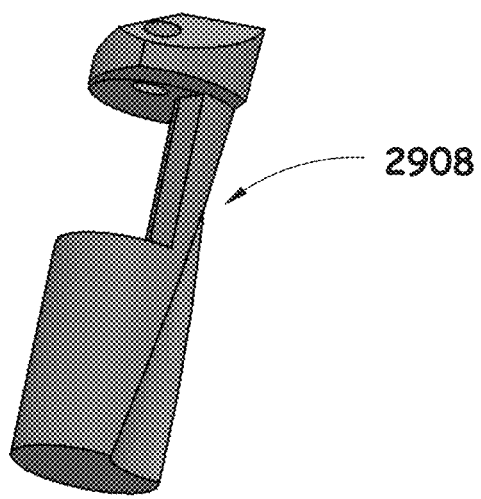

FIGS. 29A-C show an exemplary bone material removal device 2900 comprising a cutting tooth 2902 formed with a flat cutting face 2904, according to some embodiments of the invention. FIG. 29B shows the cutting tooth 2902 coupled to a rod hinge 2906, and FIG. 29C shows a shaft 2908 of device 2900 separated from the cutting tooth and hinge. A flat cutting face 2904 may apply equally distributed force, along its radial axis, on the bone material.

Figure 30A:
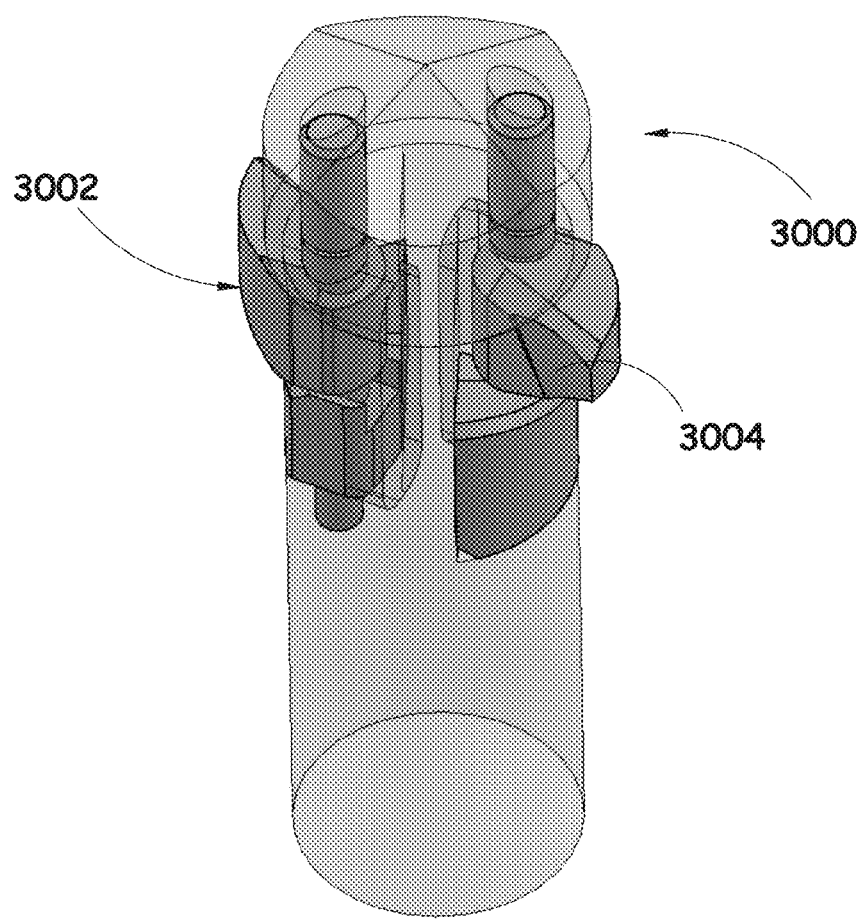
FIGS. 30A-C illustrate a bone material removal device comprising a plurality of cutting teeth, according to some embodiments of the invention.
Figure 30B:
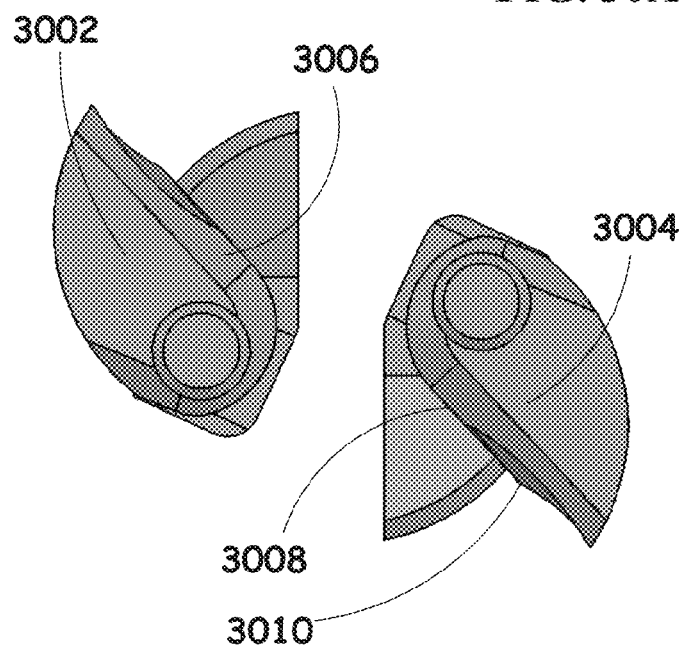
Figure 30C:
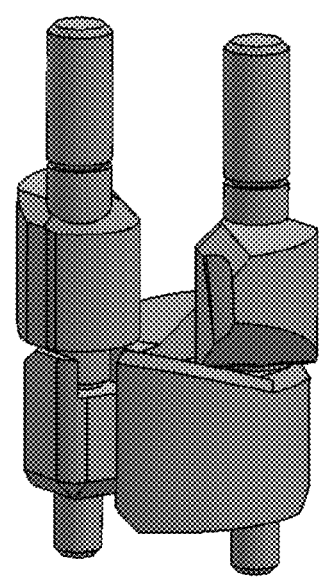

FIGS. 30A-C illustrate a bone material removal device 3000 comprising a plurality of cutting teeth, such as 2 cutting teeth, according to some embodiments of the invention. FIGS. 30B and 30C are a cross section and a side view, respectively, showing the two cutting teeth and their respective hinges separately from a shaft of device 3000, to provide a clearer view.

In some embodiments, teeth 3002 and 3004 are positioned diametrically opposing each other. Optionally, the teeth are oriented in a configuration in which their cutting faces 3006 and 3008 respectively face opposite directions. A potential advantage of widening a bore using a plurality of cutting teeth may include increasing a rate of bone material removal.

In some embodiments, for example as shown in FIG. 30B, a concavity 3010 of a cutting face is non-symmetrical, for example along a height of the tooth.

It is expected that during the life of a patent maturing from this application many relevant bone material removal device will be developed and the scope of the term bone material removal device is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A bone material removal device comprising:
   a drill bit comprising an elongated shaft having a longitudinal axis said shaft comprising one or more flutes;
   at least one bone material removal element for widening a bore in a bone, said element coupled to said shaft having a recess;
   said element movable from a closed position, in which said element is partially received within the recess of said shaft, to an open position in which said element extends radially away from said shaft by movement of said element about a longitudinal axis of said shaft, generally in a plane perpendicular to said longitudinal axis of said shaft; and
   wherein a portion of said shaft adjoining both longitudinal sides of said element defines a generally cylindrical volume of rotation, and at least a portion of said bone removal element extends radially beyond said volume of rotation when said element is in said closed position.

2. The device according to claim 1, wherein said bone material removal element is a pivotable cutting tooth coupled to said shaft by a hinge.

3. The device according to claim 2, wherein at least a portion of said cutting tooth is large enough to resist further entry of said tooth into said shaft in said closed position.

4. The device according to claim 2, wherein said cutting tooth comprises a cutting face formed with a flat portion.

5. The device according to claim 2, wherein said tooth is freely pivotable on said hinge to open as a result of reversal of rotation direction of said device.

6. The device according to claim 2, wherein said device comprises a plurality of cutting teeth.

7. The device according to claim 1, wherein said portion protrudes to a distance ranging between 0.05 mm to 0.5 mm radially from said volume of rotation when in said closed position.

8. The device according to claim 1, comprising at least one hinge extending in parallel to a longitudinal axis of said shaft, and providing for pivotable connection of said bone removal element to said shaft on two sides of said bone removal element.

9. The device according to claim 1, wherein said bone removal element extends from said shaft upon rotation due to centrifugal force.

10. The device according to claim 1, wherein said device is adapted to operate in a bore drilling configuration, having a rotation direction in which the bone removal element is in said closed position.

11. The device according to claim 1, wherein said device is adapted to operate in a bore widening configuration in which said bone removal element is in said open position, wherein the bore widening configuration is selected by selecting a direction of rotation of the device.

12. The device according to claim 1, wherein said device is cannulated.

13. A bone material removal device comprising:
an elongated cannulated shaft having a longitudinal axis;
at least one bone material removal element for widening a bore in a bone, said element coupled to said shaft having a recess;
said element movable from a closed position, in which said element is partially received within the recess of said shaft, to an open position in which said element extends radially away from said shaft by movement of said element about a longitudinal axis of said shaft, generally in a plane perpendicular to said longitudinal axis of said shaft; and
wherein a portion of said shaft adjoining both longitudinal sides of said element defines a generally cylindrical volume of rotation, and at least a portion of said bone removal element extends radially beyond said volume of rotation when said element is in said closed position.

14. The device according to claim 13, wherein said bone material removal element is at least one pivotable cutting tooth coupled to said shaft by a hinge.

15. The device according to claim 14, wherein at least a portion of said cutting tooth is large enough to resist further entry of said tooth into said shaft in said closed position.

16. The device according to claim 14, wherein said cutting tooth comprises a cutting face formed with a flat portion.

17. The device according to claim 14, wherein said tooth is freely pivotable on said hinge to open as a result of reversal of rotation direction of said device.

18. The device according to claim 13, comprising at least one hinge extending in parallel to a longitudinal axis of said shaft, and providing for pivotable connection of said bone removal element to said shaft on two sides of said bone removal element.

19. The device according to claim 13, wherein said bone removal element extends from said shaft upon rotation due to centrifugal force.

20. The device according to claim 13, wherein said device is adapted to operate in a bore drilling configuration, having a rotation direction in which the bone removal element is in said closed position or in a bore widening configuration in which said bone removal element is in said open position, wherein the bore drilling and bore widening configurations are selected by selecting a direction of rotation of the device.

* * * * *